(12) United States Patent
Melton

(10) Patent No.: US 12,303,465 B2
(45) Date of Patent: May 20, 2025

(54) APPARATUS, METHODS, AND SYSTEMS FOR POSITIONING AND RETAINING A NASALLY INTRODUCED MEDICAL TUBE TO A PATIENT

(71) Applicant: MACKEY MASK LLC, Denison, TX (US)

(72) Inventor: Tara Melton, Martinez, GA (US)

( * ) Notice: Subject to any disclaimer, the term of this patent is extended or adjusted under 35 U.S.C. 154(b) by 0 days.

(21) Appl. No.: 18/498,313

(22) Filed: Oct. 31, 2023

(65) Prior Publication Data

US 2024/0139074 A1 May 2, 2024

Related U.S. Application Data

(60) Provisional application No. 63/421,252, filed on Nov. 1, 2022.

(51) Int. Cl.
| | | |
|---|---|---|
| *A61M 16/06* | (2006.01) | |
| *A61J 15/00* | (2006.01) | |
| *A61M 25/02* | (2006.01) | |

(52) U.S. Cl.
CPC ....... *A61J 15/0061* (2013.01); *A61J 15/0003* (2013.01); *A61M 16/0683* (2013.01); *A61M 16/0666* (2013.01); *A61M 2025/0226* (2013.01)

(58) Field of Classification Search
CPC ................ A61J 15/0061; A61J 15/0003; A61J 15/0053; A61M 16/0683; A61M 25/02; A61M 16/0497; A61M 2025/022; A61M 2025/026; A61M 2240/00; A61M 16/0605; A61M 2025/0206; A61M 16/06; A61M 2025/0226; A61M 16/0666; A61M 16/0694; A61M 2025/0213; A61M 5/1418; A62B 18/084
See application file for complete search history.

(56) References Cited

U.S. PATENT DOCUMENTS

| | | | |
|---|---|---|---|
| 3,388,699 A * | 6/1968 | Webb | ................... A61N 1/0472 600/26 |
| 4,282,871 A | 8/1981 | Chodorow et al. | |
| 5,117,818 A * | 6/1992 | Palfy | ..................... A61M 25/02 128/207.18 |
| 6,523,229 B2 * | 2/2003 | Severson | ........... B65D 63/1018 24/16 PB |
| 6,536,436 B1 | 3/2003 | McGlothen | |

(Continued)

FOREIGN PATENT DOCUMENTS

| | | |
|---|---|---|
| CN | 103961775 | 8/2014 |
| CN | 207898751 | 9/2018 |

(Continued)

*Primary Examiner* — Courtney B Fredrickson
(74) *Attorney, Agent, or Firm* — Derek Fahey, Esq.; The Plus IP Firm, PLLC

(57) ABSTRACT

A medical tube securement system is disclosed, designed for securing nasally introduced medical tubes to patients. This system features a non-adhesive, non-invasive head-piece with a groove. Integrated within are a face strap and a backstay, both with grooves for tube placement. The face strap has a semi-tubular body, a cushion, and a nostril piece. The backstay is ring-shaped with a perimeter channel for tube accommodation. Enhanced grip is provided by the backstay's textured surface, and a unique tab ensures effective strap attachment.

13 Claims, 12 Drawing Sheets

(56) References Cited

U.S. PATENT DOCUMENTS

| | | | |
|---|---|---|---|
| D501,554 S | * | 2/2005 | Hansen .................. D24/128 |
| 10,874,814 B2 | | 12/2020 | Huddart et al. |
| 11,110,242 B2 | | 9/2021 | Ronayne et al. |
| 2001/0029954 A1 | | 10/2001 | Palmer |
| 2011/0308520 A1 | | 12/2011 | McAuley et al. |
| 2012/0111332 A1 | * | 5/2012 | Gusky ............... A61M 16/0666 |
| | | | 128/205.25 |
| 2012/0138060 A1 | | 6/2012 | Barlow |
| 2013/0213400 A1 | * | 8/2013 | Barlow ............. A61M 16/0622 |
| | | | 128/205.25 |
| 2013/0220327 A1 | * | 8/2013 | Barlow ............. A61M 16/0816 |
| | | | 128/205.25 |
| 2013/0298912 A1 | * | 11/2013 | Ronayne ........... A61M 16/0683 |
| | | | 128/207.18 |
| 2015/0090255 A1 | * | 4/2015 | Gulliver .............. A61J 15/0061 |
| | | | 604/179 |
| 2015/0122255 A1 | | 5/2015 | Harrison |
| 2016/0030696 A1 | * | 2/2016 | Klenner ............ A61M 16/0003 |
| | | | 128/207.18 |
| 2020/0114109 A1 | | 4/2020 | Klenner et al. |
| 2020/0114901 A1 | | 4/2020 | Klenner et al. |
| 2021/0030993 A1 | | 2/2021 | Gunaratnam et al. |
| 2021/0316101 A1 | | 10/2021 | Ng et al. |

FOREIGN PATENT DOCUMENTS

| | | |
|---|---|---|
| CN | 211245106 | 8/2020 |
| CN | 213031615 | 4/2021 |
| CN | 215426204 | 1/2022 |

* cited by examiner

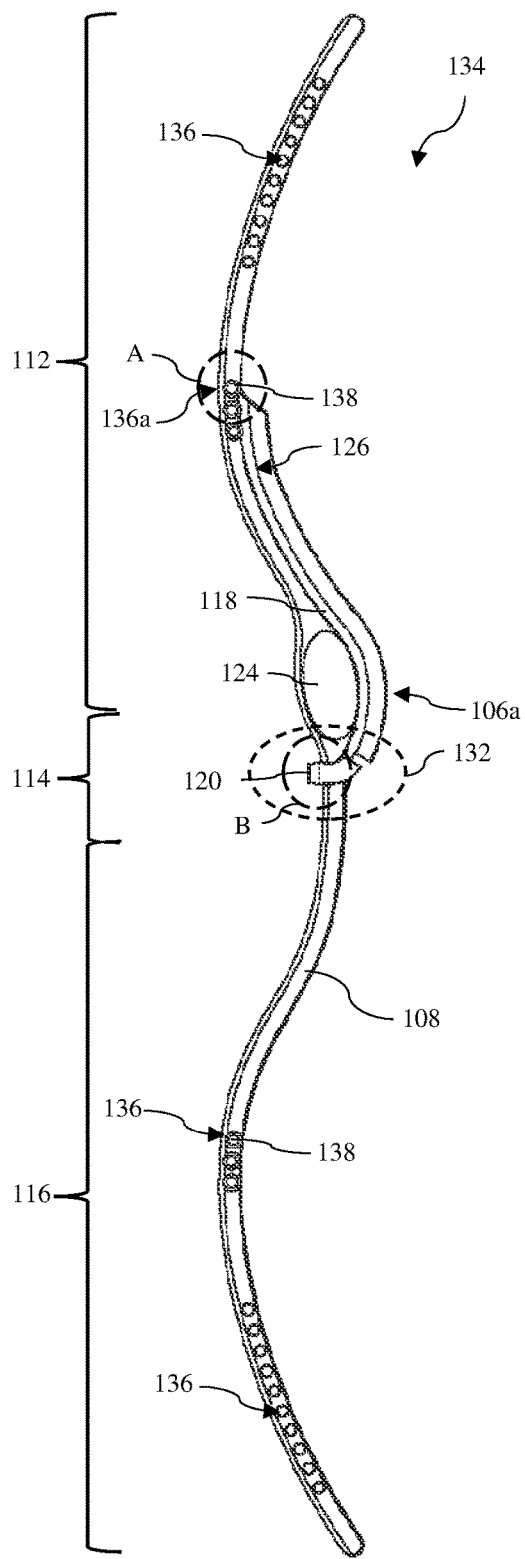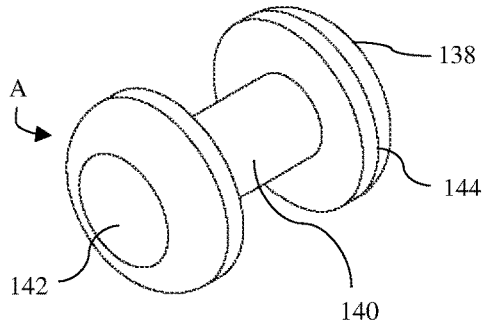
FIG. 6
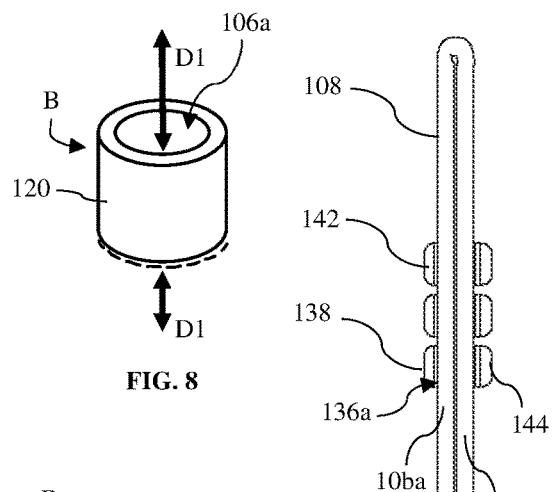
FIG. 8
FIG. 7
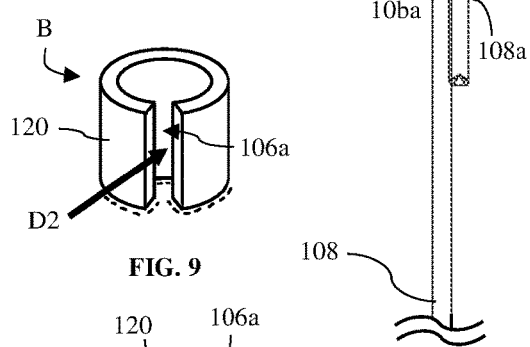
FIG. 9
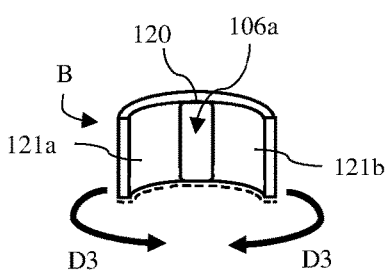
FIG. 10
FIG. 5

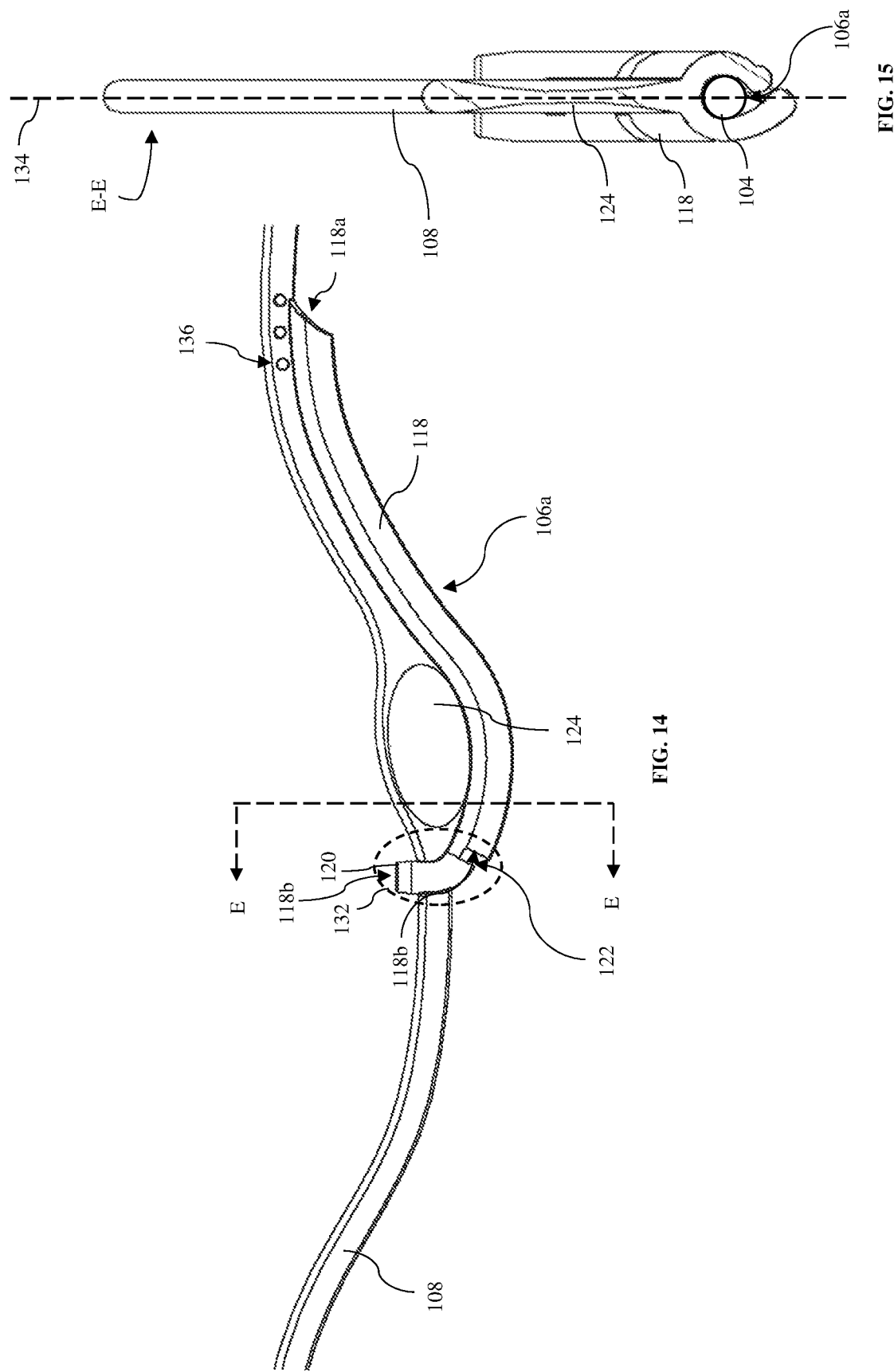

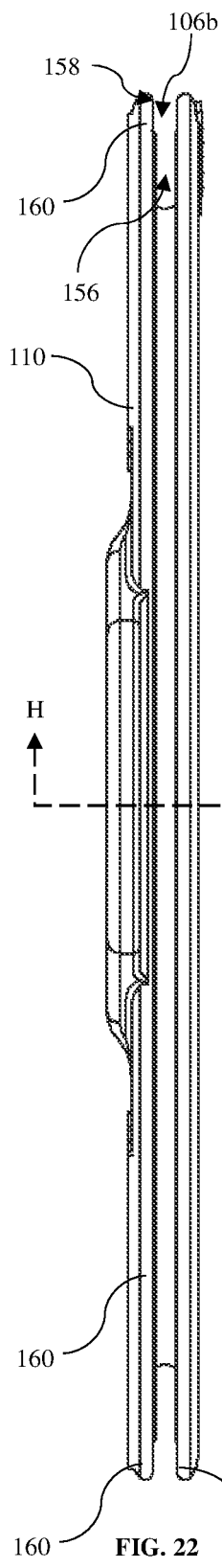
FIG. 22
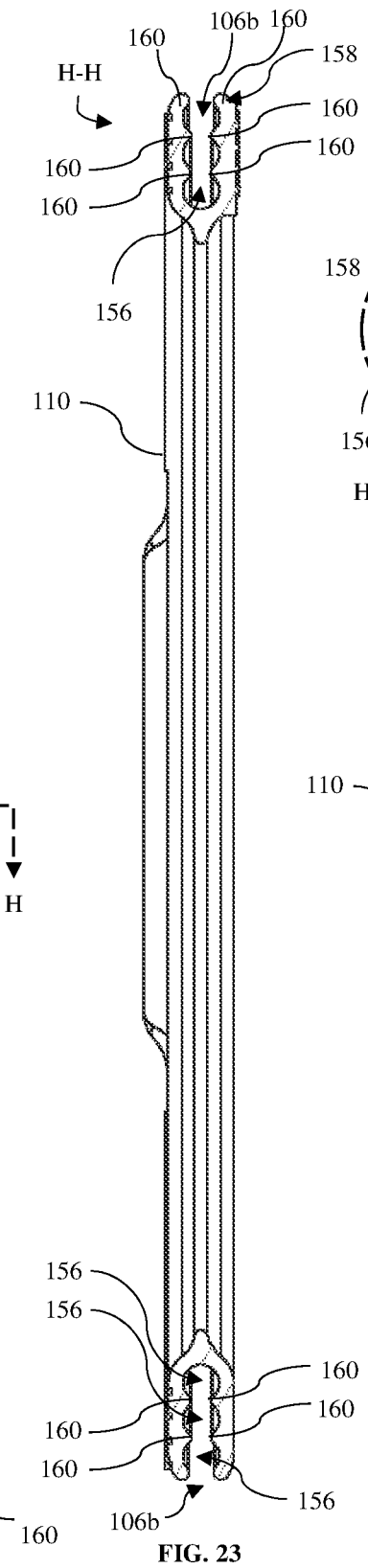
FIG. 23
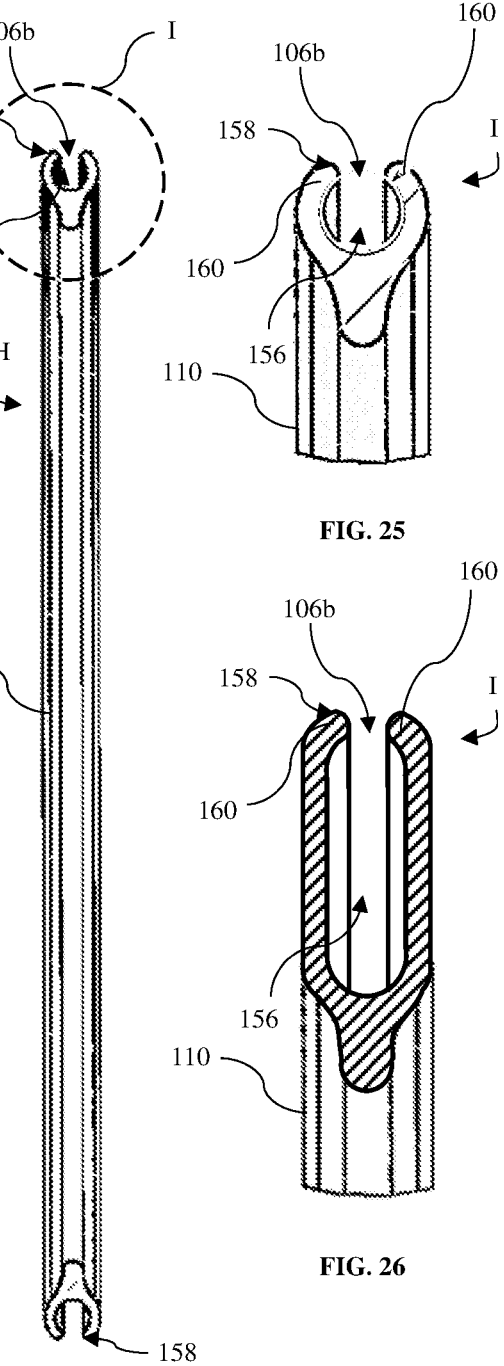
FIG. 24
FIG. 25
FIG. 26

APPARATUS, METHODS, AND SYSTEMS FOR POSITIONING AND RETAINING A NASALLY INTRODUCED MEDICAL TUBE TO A PATIENT

REFERENCE TO RELATED APPLICATIONS

This application is a non-provisional patent application claiming the benefit of U.S. Provisional Patent Application No. 63/421,252, titled "APPARATUS, METHODS, AND SYSTEMS FOR POSITIONING AND RETAINING A NASOGASTRIC OR RESPIRATORY TUBE ON A PATIENT", and filed Nov. 1, 2022, the subject matter of which is hereby incorporated by reference herein.

CROSS-REFERENCES

Not applicable.

STATEMENT REGARDING FEDERALLY SPONSORED RESEARCH OR DEVELOPMENT

Not applicable.

INCORPORATION BY REFERENCE OF MATERIAL SUBMITTED ON A COMPACT DISK

Not applicable.

TECHNICAL FIELD

The present disclosure relates to the field of medical tube securement devices, and more specifically to the field of securement systems for tubes that are introduced nasally.

BACKGROUND OF THE INVENTION

Medical tubes are an integral component of patient care across various clinical settings, ranging from acute care hospitals to home-based care. Specifically, tubes that are introduced through the nasal passage, such as nasogastric, nasointestinal, nasobiliary, and nasotracheal tubes, among others, play crucial roles in therapeutic interventions, diagnostics, and patient management.

However, the securement of these tubes presents a set of unique challenges. Improperly secured tubes can lead to complications like dislodgement, resulting in interruptions in treatment, or even aspiration in the case of feeding tubes. Such complications can lengthen hospital stays, increase healthcare costs, and most critically, pose significant risks to patient health and comfort.

Historically, various methods have been employed to secure such tubes in place. Common techniques involve the use of adhesive tapes and clamps. However, these traditional methods present several drawbacks. First, adhesive tapes, when frequently changed, can cause skin irritation or even damage, leading to discomfort and an increased risk of infection. Some patients, especially those with sensitive skin or prolonged hospital stays, can develop allergic reactions or pressure ulcers. Furthermore, adhesive residues can be challenging to remove and can trap bacteria.

When it comes to the delicate populations of infants, toddlers, and especially neonates, the securement of medical tubes becomes an even more intricate challenge. Their skin is much thinner and more sensitive compared to adults, making them more susceptible to irritation and damage. The use of adhesive tapes, commonly employed in the prior art, poses heightened risks for these age groups. A neonate's epidermis and dermis are not yet fully developed; hence adhesive removal can not only cause immediate discomfort but also lead to skin tears, increasing the risk of bacterial infections. Repetitive taping can exacerbate these effects, occasionally resulting in long-lasting scars that persist into adulthood. Moreover, allergic reactions to the chemical components of adhesives are not uncommon in neonatal intensive care units (NICUs), adding another layer of complications to an already vulnerable demographic.

Clamps, on the other hand, are traditionally employed as an alternative to adhesives for securing medical tubes, have their own set of challenges that can compromise both the tube's functionality and patient comfort. Their primary mechanism revolves around exerting force to retain the tube in position. However, this force, if not meticulously calibrated, can present a series of concerns. However, the pressure exerted by clamps can, at times, be excessive, leading to the physical deformation of the tube. Repeated or prolonged clamping can weaken the tube's structural integrity, rendering it susceptible to cracks or breaks. When the tube's structure is compromised, it can lead to internal narrowing or even occlusion. This is particularly problematic as it can hinder the free flow of fluids, gases, or medications, essentially undermining the very purpose of the tube. For certain critical applications, even a slight impedance in flow can have profound clinical implications. Such damage can precipitate tube malfunction, necessitating premature replacements and posing potential risks of leakage or contamination and infection.

Another significant problem associated with prior art is the unintentional displacement or removal of tubes. In situations where the tube is not securely fastened, movements from the patient, whether voluntary or involuntary, can lead to tube misplacement. This not only affects the tube's function but in certain cases can lead to severe complications, especially if not detected in time.

For toddlers, who are often more mobile and explorative, the risk of unintentional tube displacement becomes significant. Not only does this compromise the tube's function, but the repeated application and removal of adhesives to re-secure tubes can intensify skin damage. Over time, this repeated trauma can culminate in hypertrophic or keloid scars, which might require medical intervention for correction.

In adult patients, particularly those who are intubated or under the influence of medications leading to disorientation or confusion, tube securement presents a distinct set of challenges. The combination of physical discomfort, the foreign sensation of intubation, and the cognitive effects of certain drugs can result in heightened agitation. Such a state increases the likelihood of inadvertent tube removal or displacement, which can have life-threatening consequences.

Intubation, necessary for ensuring the airway remains open or for mechanical ventilation, is an invasive procedure that, while crucial, can be a significant source of discomfort. An improperly secured endotracheal or tracheostomy tube can rub against the skin or mucosal linings, leading to irritation, ulcers, or even infections. Such discomfort can prompt even the most passive patients to instinctively reach for and pull at the tubes, particularly when their cognitive abilities are compromised by medications or underlying conditions.

Furthermore, for those patients who are disoriented or confused, the presence of a foreign object like a tube can be immensely distressing. They may not understand its purpose or the implications of removing it, and their primary instinct might be to eliminate the source of their discomfort, potentially leading to self-inflicted harm or compromising their medical treatment. If a patient removes an essential tube, such as one used for ventilation, the result can be rapid deoxygenation and, in severe cases, death.

Beyond the physical repercussions, there are also psychological implications to consider. Painful experiences during infancy and toddlerhood, such as those associated with tube securement and the resulting skin issues, can lead to increased anxiety and stress during future medical procedures. This can pose challenges for caregivers and medical professionals in ensuring both the physical and emotional well-being of the child.

Furthermore, the process of adjusting, removing, or replacing tubes with the previously mentioned systems can be cumbersome, time-consuming, and might require more than one healthcare professional, especially in cases of agitated or non-cooperative patients. In home care settings, the challenges are compounded. Many patients who rely on nasogastric or respiratory tubes at home may not have constant access to trained medical professionals. Instead, the responsibility of tube management often falls on family members or caregivers who might not have comprehensive medical training. For these non-medical professionals, the intricacies of tube adjustments or replacements using traditional securement methods can be daunting. They may feel anxious about accidentally causing discomfort to the patient or dislodging the tube, which could lead to severe medical consequences. Moreover, in emergency situations, when a tube becomes dislodged or compromised, waiting for a healthcare professional to arrive and rectify the situation isn't always feasible. This places immense pressure on home caregivers to act quickly and correctly, which can be a stressful experience given the potential risks involved.

Overall, the traditional methods of securing tubes, predominantly adhesive tapes, and clamps, often don't offer the required level of security for such scenarios. Adhesives can loosen over time or with moisture, and clamps can become dislodged with sufficient force. Moreover, these methods themselves can be sources of discomfort, exacerbating the patient's distress.

Given these complexities, there is a pronounced need for an innovative securement system tailored for tubes introduced through the nasal passage. Such a system should not only ensure effective tube positioning but also prioritize patient comfort and skin health, across all age demographics.

BRIEF SUMMARY OF THE INVENTION

A securement system for positioning and retaining nasally introduced medical tubes to a patient is disclosed. This Summary is provided to introduce a selection of disclosed concepts in a simplified form that are further described below in the Detailed Description including the drawings provided. This Summary is not intended to identify key features or essential features of the claimed subject matter. Nor is this Summary intended to be used to limit the claimed subject matter's scope.

In one embodiment, a medical tube securement system is disclosed. The system comprises a head-piece with a groove tailored to hold medical tubes, ensuring that they are positioned correctly without the use of invasive or adhesive methods. Additionally, the head-piece incorporates a face strap with a semi-tubular shaped body that can be placed on either side of the patient's face, allowing for adaptability. A nostril piece is situated in the middle portion of the strap, while a cushion is positioned proximate to the semi-tubular body, ensuring patient comfort. Furthermore, the securement system includes a backstay featuring a ring-shaped body with a second groove designed to further secure the tube. The combination of these components ensures that nasally introduced tubes are held securely and comfortably, minimizing the risk of dislodgement, and reducing skin irritation.

Additional aspects of the disclosed embodiment will be set forth in part in the description which follows, and in part will be obvious from the description, or may be learned by practice of the disclosed embodiments. The aspects of the disclosed embodiments will be realized and attained by means of the elements and combinations particularly pointed out in the appended claims. It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute part of this specification, illustrate embodiments of the disclosure and together with the description, explain the principles of the disclosed embodiments. The embodiments illustrated herein are presently preferred, it being understood, however, that the disclosure is not limited to the precise arrangements and instrumentalities shown, wherein:

FIG. 5 is a front view of a face strap of the medical tube securement system, according to an example embodiment;

FIG. 6 is a detailed view of a fastener of the face strap, according to an example embodiment;

FIG. 7 illustrates a portion of the face strap attached to the fastener, according to an example embodiment;

FIG. 8 illustrates a detailed view of a nostril piece, according to an example embodiment;

FIG. 9 illustrates a detailed view of the nostril piece, according to another example embodiment;

FIG. 10 illustrates a detailed view of the nostril piece, according to another example embodiment;

FIG. 14 is a front view of the face strap showing a semi-tubular shaped body and a cushion, according to an example embodiment;

FIG. 15 is a cross-sectional view thereof showing the groove of the semi-tubular shaped body, according to an example embodiment;

FIG. 22 is a side of the backstay, according to an example embodiment;

FIG. 23 is a first cross-sectional view thereof, according to an example embodiment;

FIG. 24 is a second cross-sectional view thereof, according to another example embodiment;

FIG. 25 is a first detailed view thereof, according to an example embodiment;

FIG. 26 is a second detailed view thereof, according to another example embodiment;

Figure 1:
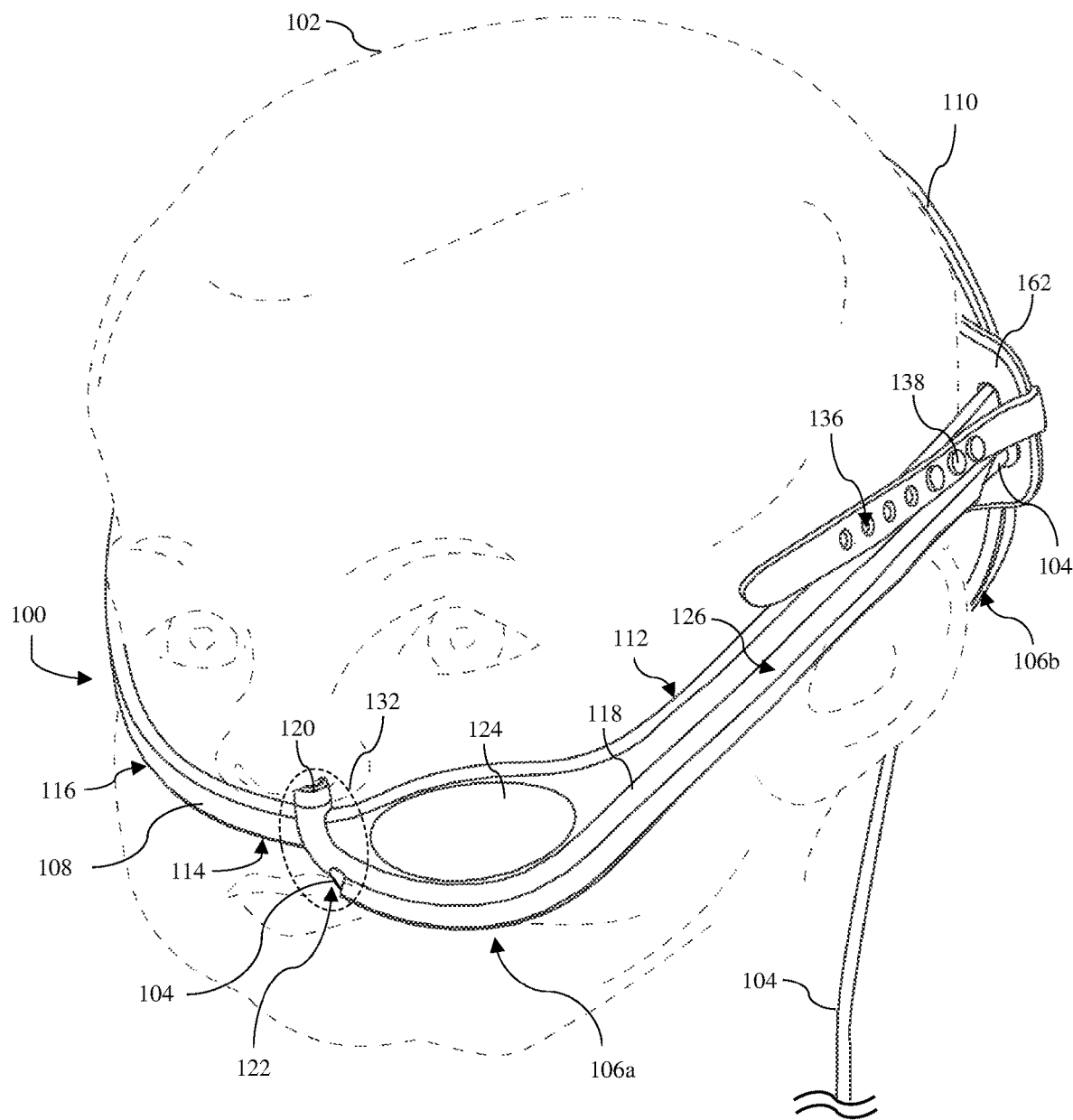
FIG. 1 is a perspective view illustrating a medical tube securement system positioned on a patient having a nasally inserted medical tube, according to an example embodiment.
Figure 2:
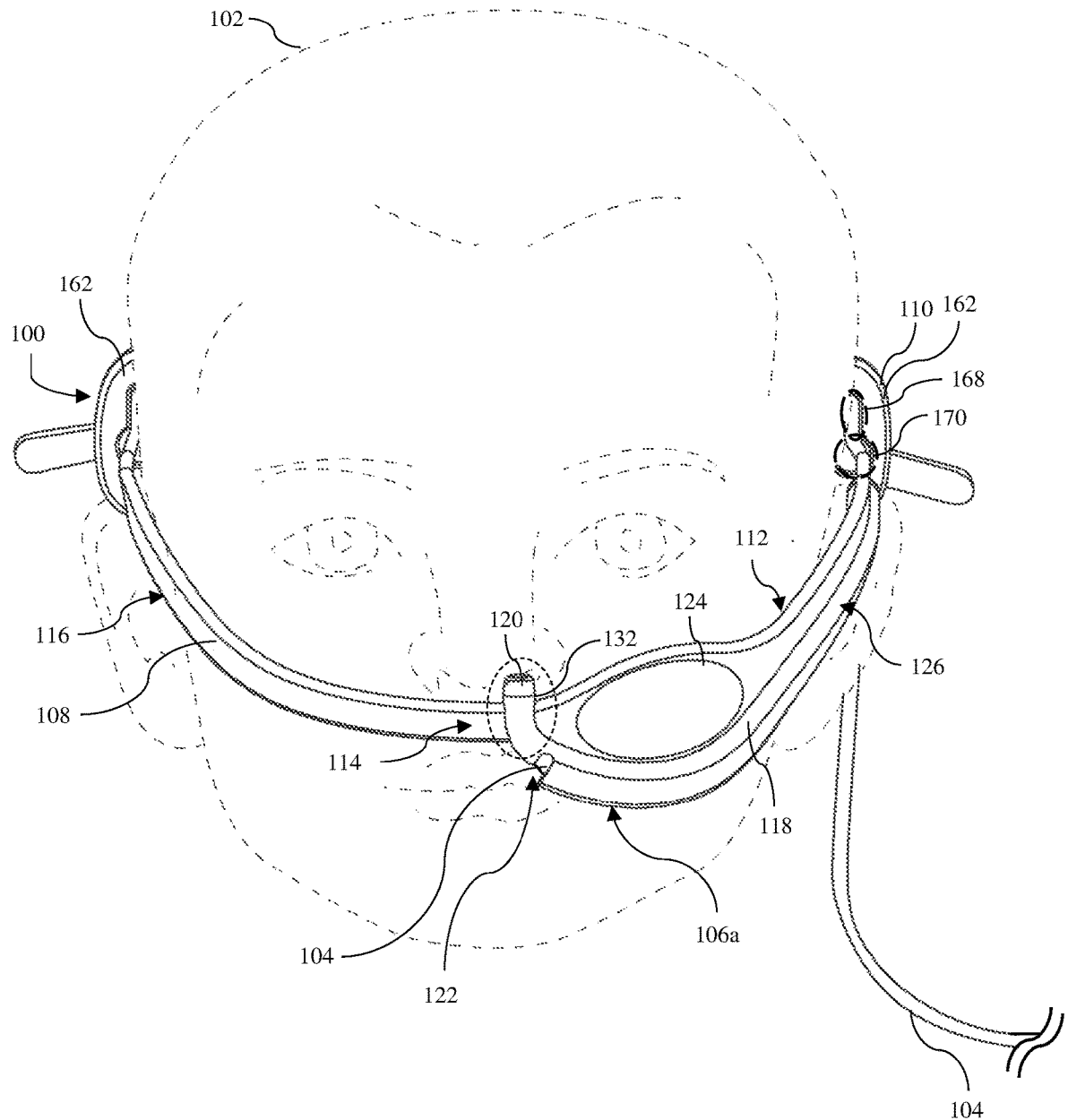
FIG. 2 is a front view thereof, according to an example embodiment.
Figure 3:
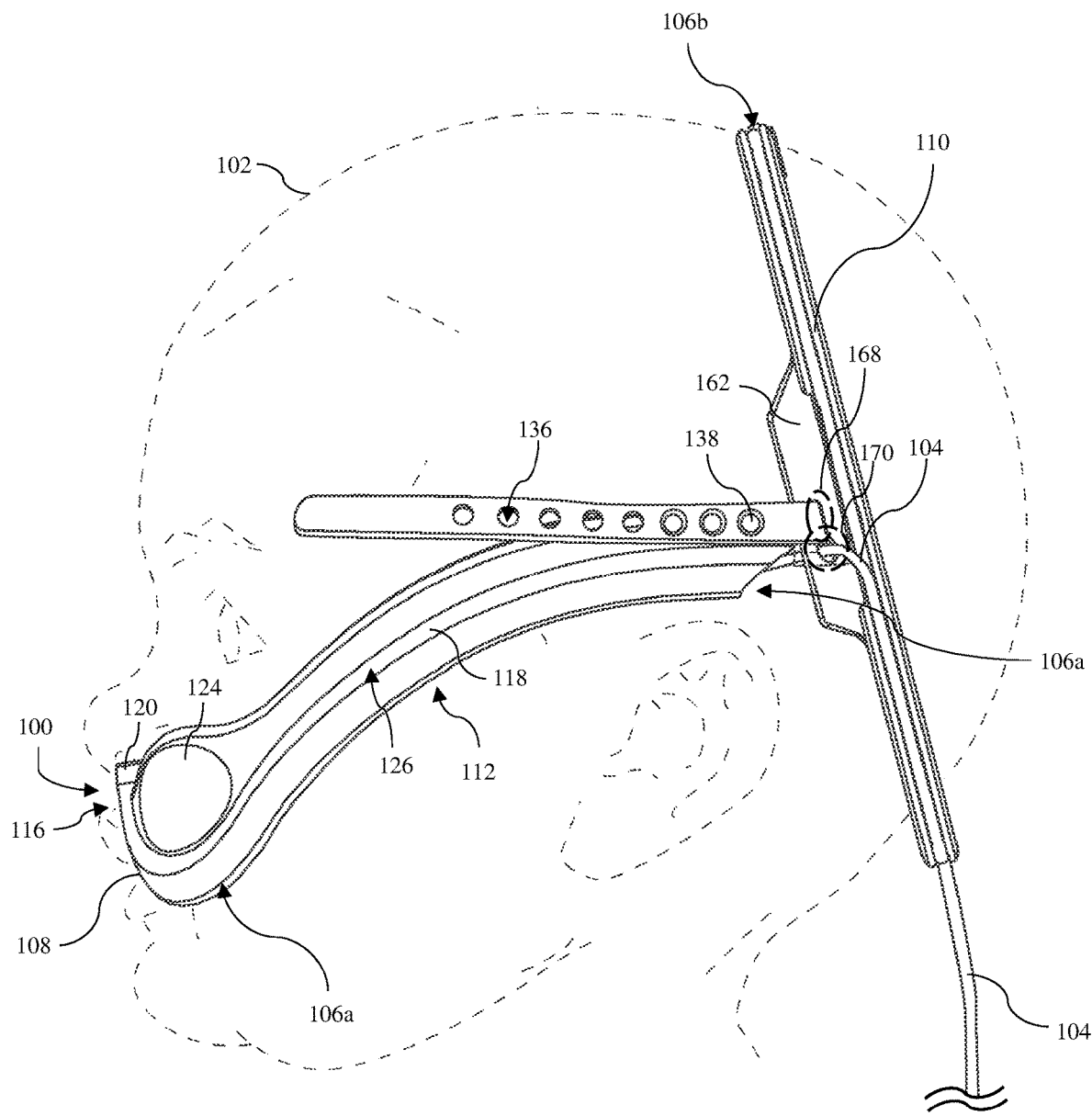
FIG. 3 is a side view thereof, according to an example embodiment.
Figure 4:
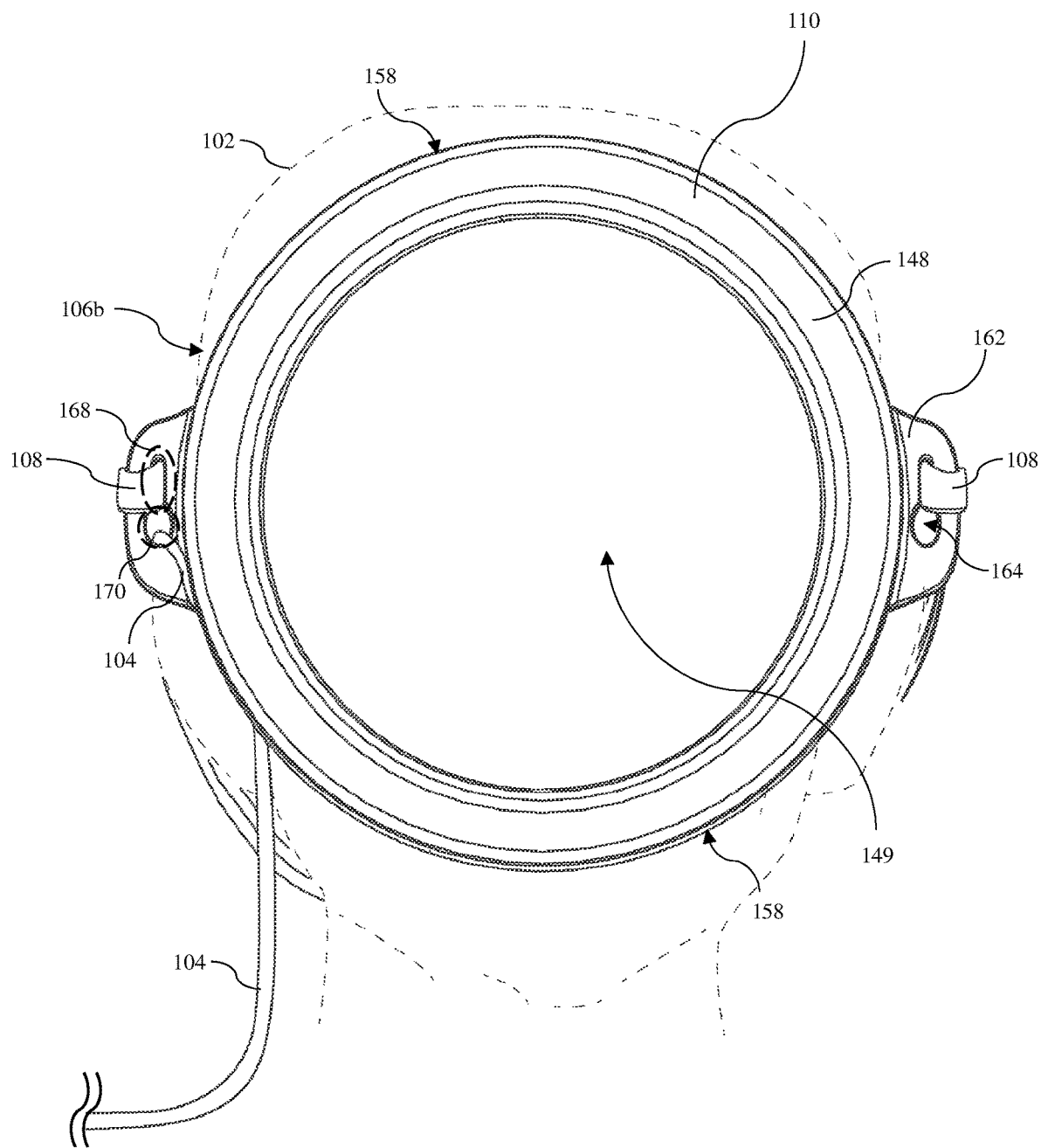
FIG. 4 is a rear view thereof, according to an example embodiment.
Figure 11:
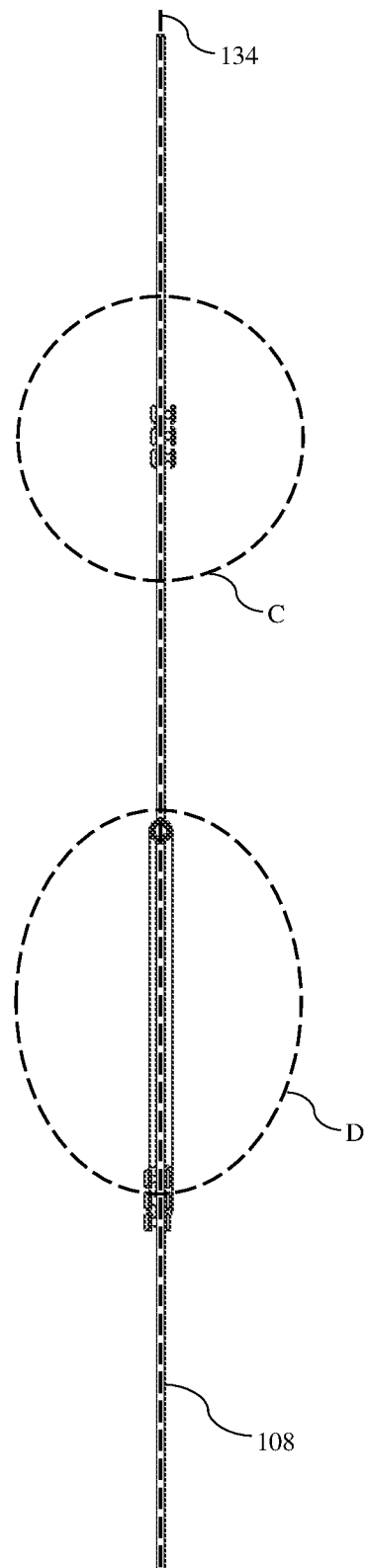
FIG. 11 is a top view of the face strap illustrating the symmetry of the face strap, according to an example embodiment.

The drawings accompanying this disclosure serve as illustrative examples of certain embodiments, demonstrating various aspects of the invention. It is important to note that these drawings, while providing valuable visual representation, are not exhaustive and do not limit the scope of the invention. Other embodiments that fall within the spirit and scope of the invention may be included, whether they are explicitly interpreted, perceived, or anticipated by the appended claims. The drawings are too scale, ensuring that the visual representation accurately reflects the proportions and relationships among components, further enhancing their utility in understanding the invention's design and functionality.

DETAILED DESCRIPTION

The following detailed description refers to the accompanying drawings. Whenever possible, the same reference numbers are used in the drawings and the following description to refer to the same or similar elements. While disclosed embodiments may be described, modifications, adaptations, and other implementations are possible. For example, substitutions, additions, or modifications may be made to the elements illustrated in the drawings, and the methods described herein may be modified by substituting reordering or adding additional stages or components to the disclosed methods and devices. Accordingly, the following detailed description does not limit the disclosed embodiments. Instead, the proper scope of the disclosed embodiments is defined by the appended claims.

The disclosed embodiments improve upon the problems with the prior art, particularly addressing the inherent shortcomings often encountered in previous tube securement methodologies. Foremost among these advancements is the non-adhesive, non-invasive mechanism of securement afforded by the distinctively designed head-piece, which possesses a tailored groove for the meticulous retention of medical tubes. Such a design obviates the historical reliance on adhesive tapes, frequently implicated in skin irritations and adverse allergic reactions.

The integration of the semi-tubular groove addresses the practical challenges often associated with medical tube placement. In traditional methods, the application of tubes often necessitates the use of adhesives, primarily due to their ease of use. However, adhesives, while convenient, come with a suite of complications, from skin irritations to potential allergic reactions. The semi-tubular groove, in stark contrast, offers a seamless application process, providing a secure hold without the drawbacks associated with adhesives. This design choice not only streamlines the placement process but also circumvents the adverse reactions commonly linked to adhesive compounds.

The face strap's symmetry affords clinicians the flexibility to position the semi-tubular body on either the patient's left or right facial side. Such versatility not only conforms to patient-specific anatomical nuances but also caters to unique clinical preferences or constraints. The symmetrical face strap allows healthcare professionals to effortlessly reposition the strap on either side of a patient's face, thereby mitigating the risk of localized skin irritations or sores that can arise from prolonged pressure or friction in a singular area. This strategic capability ensures that skin health is maintained, even in scenarios of extended tube placements.

Emphasizing patient-centric considerations, the incorporation of a strategically placed cushion proximate to the semi-tubular body serves to alleviate potential pressure-induced discomfort, a concern that becomes paramount in scenarios of extended tube placement durations.

The backstay, characterized by its ring-shaped anatomy and supplemented by a secondary groove, epitomizes robustness in tube retention. Such a groove is particularly adept at countering inadvertent tube dislodgements, a frequent challenge in scenarios with agitated or non-compliant patients. In addition, catering to the anatomical diversity among patients, the ring-shaped halo or backstay exhibits versatility that allows it to comfortably accommodate a wide range of head shapes and sizes. This ensures that the securement system remains steadfast and comfortable irrespective of the patient's unique head contour, enhancing the overall user experience.

Moreover, the embodiment underscores simplicity in its application and management protocols, positioning it as an ideal solution not just for clinical settings but also for home care scenarios, where non-medical professionals might be tasked with tube adjustments. By circumventing adhesive modalities and integrating elements that prioritize comfort, this system showcases a profound commitment to preserving skin integrity, thereby significantly curtailing the risk of lasting scars or other dermatological adversities that are often an inadvertent byproduct of traditional securement techniques. Collectively, these inventive facets render the disclosed system a paradigm shift in tube securement, marrying clinical efficacy with unparalleled patient comfort across diverse care environments.

In comparison to the prior art that utilizes a unitary construction, the disclosed headpiece, bifurcated into two distinct components, namely, the strap and the backstay, presents a remarkable advancement in design and functionality. Historically, unitary headpieces mandate the mask to be maneuvered over or onto the user's head, an act which frequently necessitates the exertion of undue force or intricate repositioning of the head for proper fitment. Such actions, especially in clinical or medical environments, can pose significant risks. For patients with neck or spinal injuries, traumatic brain injuries, or certain surgical interventions, any unnecessary movement or manipulation of the head can exacerbate injuries, leading to further complications or discomfort. Moreover, the act of drawing a unitary headpiece over the head can produce undue constriction, which may impede proper circulation, cause headaches, or even exacerbate pre-existing conditions. The disclosed headpiece, by virtue of its two-part construction, ameliorates these challenges. It allows for expedient assembly and fitting without obliging the user to engage in any excessive head movements or endure undue force. In essence, the headpiece can be comfortably and safely positioned around the patient's head without the drawbacks and dangers associated with pulling a unitary structure over it. As such, this innovative design not only bolsters user comfort but also introduces an elevated degree of safety, especially pivotal for vulnerable patients, distinguishing it substantially from traditional designs.

Lastly, the choice of material further underscores the invention's commitment to patient comfort and safety. In one embodiment, crafted from lightweight, thin, medical-grade silicone, the securement system is delicate to the touch yet robust in function. Silicone, known for its hypoallergenic properties and adaptability, conforms gently to the skin, reducing the likelihood of irritation while ensuring optimal tube retention. This combination of material excellence and innovative design positions the disclosed invention as a trailblazer in the realm of medical tube securement, offering an unparalleled blend of functionality, comfort, and patient safety.

Referring now to the Figures, FIGS. 1 through 4 provide detailed visual representations of the head-piece 100 as secured on a patient 102. Generally, a head-piece refers to an object or accessory designed to be worn on or around the head. Specifically, in the context of the medical tube securement system as described in the provided claims, a head-piece is a component designed to secure a medical tube 104 to a patient. A medical tube is a flexible hollow structure used in various medical procedures to transport fluids, gases, or act as a conduit for instruments or other devices. Medical tubes can be inserted into various parts of a patient's body for diagnostic, therapeutic, or monitoring purposes. More specifically, within the scope of the present disclosure, a medical tube pertains to specialized conduits purposefully designed for introduction through the nasal passages to facilitate various medical applications. These nasally inserted medical tubes, while encompassing a broad spectrum, are primarily characterized by their strategic deployment within the nasal cavities, taking into consideration the anatomical intricacies and sensitivities inherent to this region. By way of non-limiting examples, such tubes may include nasogastric tubes, for administering nutrition or medication directly to the stomach, nasoenteric tubes, reaching into the small intestine, and nasotracheal tubes, used for respiratory support in certain intubation procedures.

This head-piece incorporates a groove (106a, 106b) for securing the medical tube. A groove, in its broadest sense, refers to a long, narrow cut or indentation in a surface. The groove can be shallow or deep, wide, or narrow, and can be shaped to fit a specific profile or object. Within the context of the present disclosure and as applied to the head-piece of the medical tube securement system, a groove (106a or 106b), is an elongated depression or channel, strategically integrated into the construct of the face strap 108 and backstay 110, respectively. Said groove is tailored to securely accommodate and retain medical tubes, thereby ensuring their steadfast positioning on the patient. The specific dimensions, contour, and depth of the groove have been meticulously designed to provide optimal engagement with the medical tubes, thereby preventing inadvertent dislodgment or displacement.

In accordance with the embodiments described herein, the head-piece serves as a pivotal component of the disclosed medical tube securement system. This head-piece is structured to enhance both patient comfort and tube stability. Overall, the headpiece is characterized by being non-adhesive and non-invasive, thereby providing a means to affix the tubes without causing discomfort or harm to the patient. In the context of the present disclosure, when referring to the head-piece as being non-invasive, it is intended to convey that the said component, during its utilization, does not penetrate, pierce, or otherwise intrude into the body's internal structures or cavities. In essence, the head-piece ensures that it remains external to the patient's body, thereby reducing the risks associated with internal placements, such as infections or tissue damage.

Similarly, when denoting the head-piece as non-adhesive, it is intended to underscore the absence of any sticky or adhesive materials or coatings that typically adhere to the skin or other surfaces. This characteristic is particularly salient, as the challenges posed by adhesive systems in prior art include potential allergic reactions, skin irritation, residual residue upon removal, and reduced efficacy in the presence of sweat or moisture.

The confluence of these non-invasive and non-adhesive features, as manifested in the present head-piece, proffers notable improvements over the prior art. Specifically, it provides for a safer, more comfortable, and user-friendly interface for both the patient and healthcare professionals. By eschewing the limitations and pitfalls of invasive placements and adhesive engagements, the head-piece in the present invention amalgamates efficiency with patient comfort, thereby optimizing the overall efficacy and user experience of the medical tube securement system. Moreover, it is noteworthy that the teachings of the present disclosure explicitly and intentionally diverge from, or teach away from, the prevalent reliance on adhesive and invasive securement means in prior art. Such an intentional deviation underscores the significance of the disclosed system in its pursuit to address the inherent challenges and limitations presented by traditional adhesive and invasive methods.

In exemplary embodiments, the head-piece is constructed primarily from a lightweight, medical-grade silicone, imparting a combination of flexibility, durability, and biocompatibility ideal for extended contact with a patient's skin. Such a silicone material is especially beneficial given its hypoallergenic properties, reduced risk of skin irritation, and its adaptability to conform to various contours of the patient's face. While medical-grade silicone serves as the preferred material in the embodiment described, it is contemplated that alternative embodiments of the head-piece can be fabricated from a variety of other biocompatible materials suitable for medical applications. Non-limiting examples of such alternative materials may include, but are not limited to, thermoplastic elastomers, polyurethane, latex, flexible PVC, and other biocompatible polymers or composites. Each of these materials, when utilized, should be chosen based on considerations of patient comfort, desired durability, flexibility, and the specific medical application at hand.

Integral to its configuration, the head-piece features a face strap 108. A face strap is typically a band or belt designed to be placed over or around the face, often used to secure or stabilize an object or device against the face. It may be adjustable and is typically designed for comfort and to avoid causing harm or undue pressure to the facial skin or features.

Specifically, in at least one example embodiment, the face strap 108 is a component of the medical tube securement system having a shape to contour to the nuanced anatomical features of a patient's face. The face strap 108 is incorporated with a strategically positioned first groove 106a to secure and hold medical tubes in proximity to the patient's facial region. This groove 106a securely accommodates and holds medical tubes in place, ensuring unwavering positioning irrespective of patient movements.

In tandem with the face strap, the head-piece also incorporates a backstay 110, providing additional anchorage by comfortably aligning with the posterior portion of a patient's head. The backstay 110 incorporates a second groove 106b, further reinforcing the system's capability to manage and position medical tubes. Together, the face strap 108 and backstay 110, each with their respective grooves, converge to present a holistic solution, adeptly addressing the challenges of medical tube securement.

Referring now to FIGS. 5 through 16, the face strap 108 is shown according to example embodiments. For purposes of clarity and to provide a structured description, the face strap 108 has been delineated into the first side portion 112, the middle portion 114, and the second side portion 116. However, it is pivotal to understand that such partitioning serves merely as a frame of reference tailored for the disclosed embodiment and in no way should be construed as restrictive or exhaustive. In fact, as illustrated in the exemplary embodiment within the figures, the face strap is portrayed as a cohesive, uniform strap, devoid of any discernible demarcations between its portions, underscoring the continuum and seamlessness of its construction.

The first side portion 112, refers generally to a segment or section of the face strap 108, typically positioned on one lateral side of the face strap. In a non-limiting embodiment, the first side portion 112 can be understood as that part of the face strap which, when operatively positioned, might reside on one side of a patient's face, helping to secure or maintain the orientation of the face strap. While specific dimensions and configurations may vary, the essential functional characteristic of the first side portion is to facilitate the positioning and securing of the face strap in relation to the patient's face and any nasally inserted medical tubes.

The middle portion 114, refers generally to the central segment or section of the face strap 108, typically positioned between the first and second side portions. In a non-limiting embodiment, the middle portion 114 can be understood as that part of the face strap which, when operatively positioned, might align with, or reside over the nasal bridge or adjacent regions of a patient's face. This central alignment aids in facilitating the retention and securement of nasally introduced medical tubes. While the specific dimensions, configurations, and exact positioning can vary among embodiments, the fundamental functional characteristic of the middle portion is to ensure stability and provide a foundation for the incorporation or connection of other components, such as the nostril piece 120.

The second side portion 116, refers generally to a segment or part of the face strap 108 that is typically positioned laterally opposite the first side portion. When the face strap 108 is operatively positioned on a patient, the second side portion 116 might be situated proximate to or aligning with a lateral aspect of the wearer's face, such as an area adjacent to a cheek or temple. Its primary role can include aiding in the retention and balanced securement of the face strap to ensure uniform pressure distribution and avoid undue stress on the nasally introduced medical tubes. The exact dimensions, configurations, and positioning of the second side portion can vary based on design preferences and user requirements but its primary function remains consistent across embodiments.

The strap 108 includes a semi-tubular shaped body 118, which integrally comprises the first groove 106a. This semi-tubular configuration is adeptly structured to cradle and secure the medical tube, ensuring its stability and preventing unwanted movement. It is to be appreciated that the semi-tubular shaped body is disposed along a part of the strap, and, in the embodiment disclosed, it extends across at least one of the first side portion 112 and the second side portion 116, ensuring that the medical tube is securely held in place over a significant length of its course. Furthermore, this semi-tubular shaped body seamlessly extends to the middle portion 114, providing a contiguous and uninterrupted groove 106a that facilitates smooth positioning and repositioning of the nasally introduced medical tube, while ensuring it remains in its intended location during use.

The semi-tubular shaped body is a structure that takes on a half-cylindrical or substantially half-cylindrical shape, as detailed in FIG. 15, which is characterized by a curved or arcuate surface transitioning into a flat or substantially flat surface, resembling a tube that has been split or divided along its length. FIG. 15 is a cross sectional view of FIG. 14 about the line denoted E-E. In the context of the present disclosure, the semi-tubular shaped body 118 is adeptly formed to possess a curved or arcuate surface juxtaposed with a flat or substantially flat surface, structured to cradle, and securely accommodate a medical tube. The configuration of the semi-tubular shaped body provides a guiding groove, especially along the length where it's present, facilitating ease of tube placement and adjustment. The transition from the flat surface to a bifurcated, cleaved, or fissured segment demarcates the entrance of the first groove 106a. This groove 106a navigates through the hollow core of the semi-tubular shaped body, serving as a channel for secure tube placement.

The strap 108 further incorporates a nostril piece 120. The nostril piece generally refers to a structural component, often seen in medical or health-related apparatuses, tailored to interface with, align adjacent to, or provide support in the vicinity of the nostril or nostrils of a user or patient. This piece is typically designed to ensure comfort, stability, and effective functionality, especially when employed in tandem with devices or systems that involve nasal insertion or intervention. The nostril piece may further be defined as a component of the strap specifically structured to be proximate to the location where a medical tube enters the nostril, ensuring secure positioning and enhanced comfort for the patient. Depending on its embodiment, the nostril piece 120 may be an integral part of the semi-tubular shaped body 118, a removable component, or any other variation as disclosed. Its primary function is to augment the securement of nasally introduced medical tubes, reducing potential movement or displacement, and consequently minimizing patient discomfort.

This nostril piece is disposed within the middle portion 114 of the strap and is characterized by at least a substantially enclosed tubular shaped body. The term "substantially" conveys a degree of approximation, suggesting that while the nostril piece might not be entirely enclosed, it is enclosed to such an extent that it serves its primary functional objective. Specifically, this substantially enclosed nostril piece provides a circumscribing grip around the medical tube, enhancing stability and security. Such a configuration ensures that the tube is less likely to experience lateral movements, unintentional dislodgement, or shifts that might compromise its intended positioning. By encircling a significant portion of the tube's circumference, the nostril piece effectively combats the challenges of instability, offering both the patient and the healthcare provider greater confidence in the reliability and steadfastness of the tube's placement.

The positioning of the nostril piece is strategically oriented to be proximate to the entry point where the medical tube inserts into the patient's nostril. The presence of the nostril piece not only offers an added layer of stability for the tube but also acts as a landmark or guide for correct positioning, ensuring that the tube aligns accurately with the nasal entrance without causing undue discomfort or misalignment.

Figure 28:
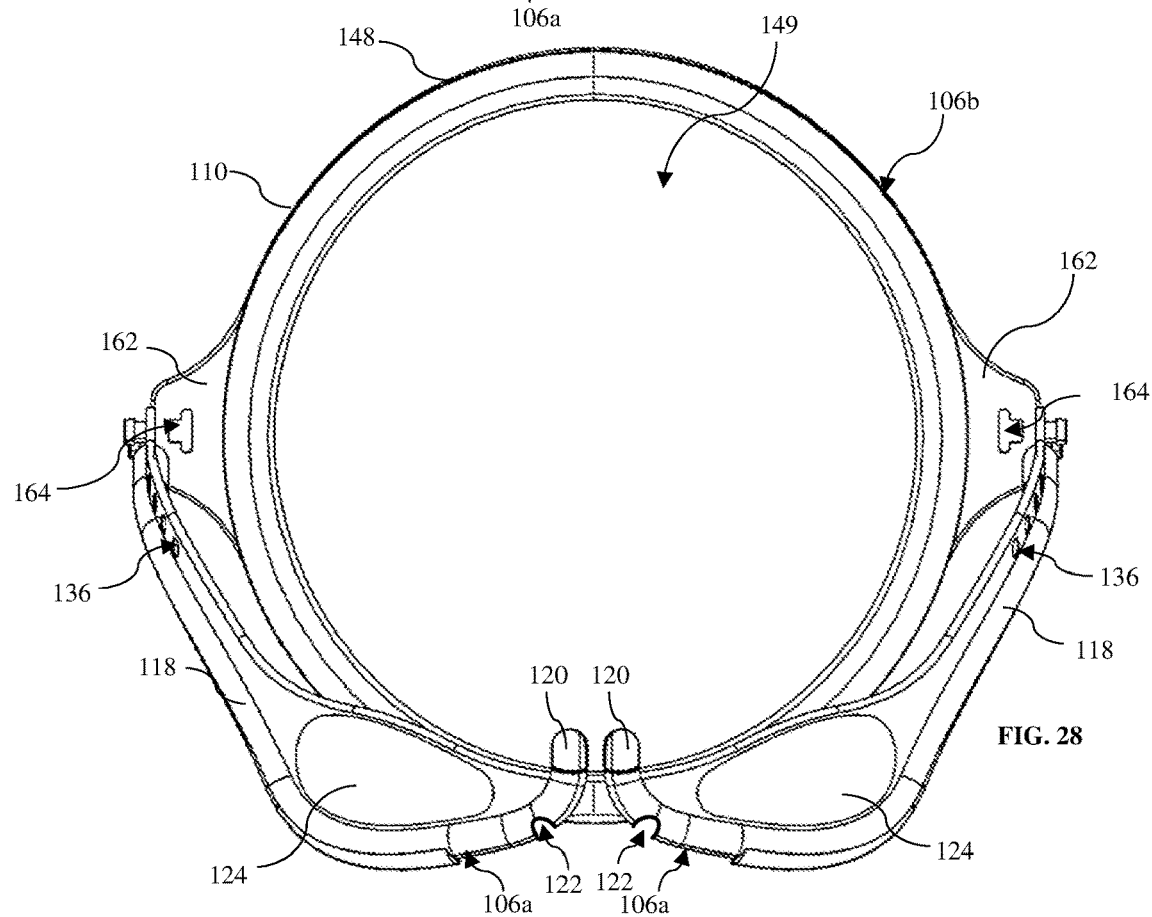
FIG. 28 is a front view of the medical tube securement system, according to another example embodiment.
Figure 29:
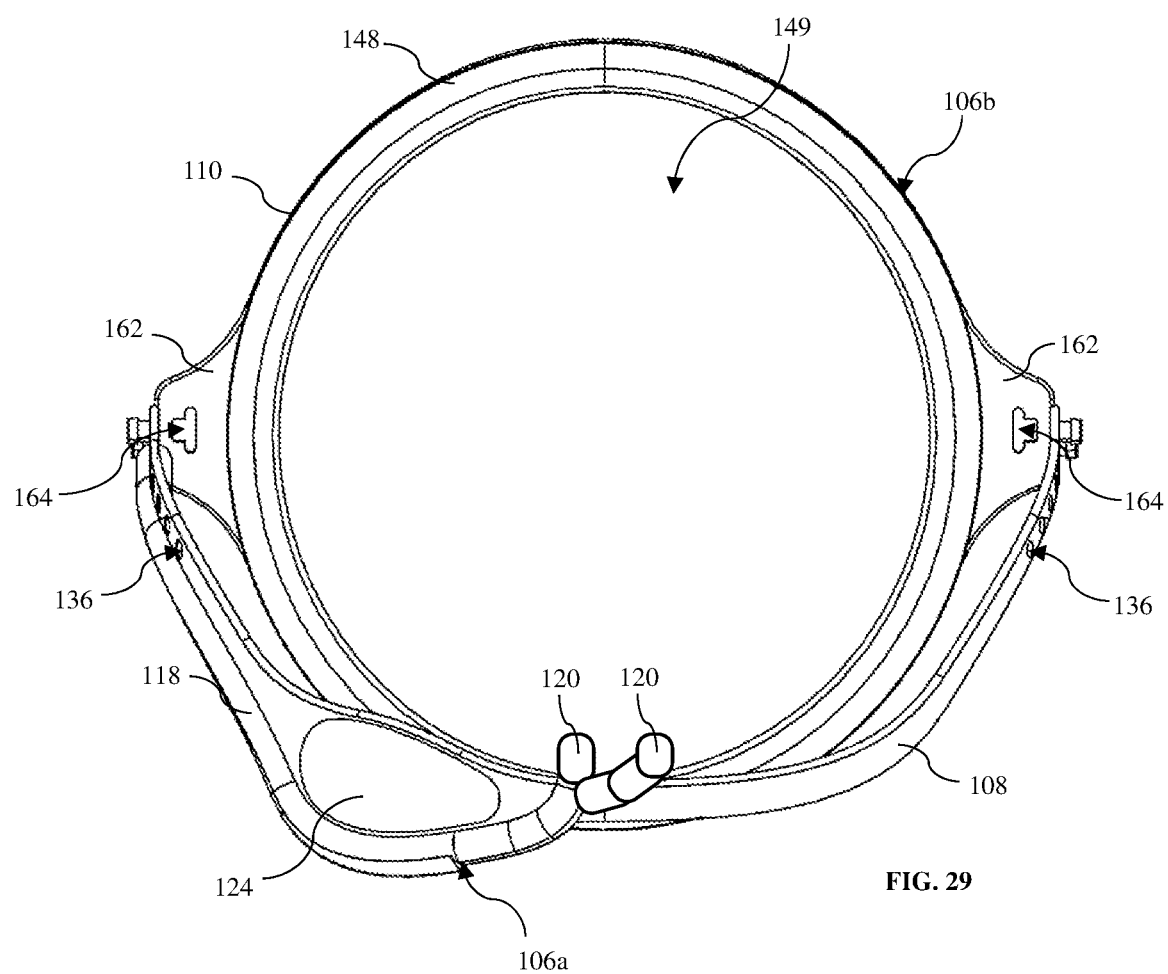
FIG. 29 is a front view of the medical tube securement system, according to another example embodiment.

In one embodiment, the nostril piece 120 is conceived as a detachable and interchangeable component that conveniently attaches to the strap 108 and the semi-tubular shaped body 118. The versatility, modularity, and interchangeability of this embodiment caters to various medical scenarios, some of which might necessitate direction into one or both nostrils. For instance, the Bilateral Nasal Cannula, an apparatus used for delivering oxygen, employs two distinct prongs or tubes specifically tailored for each nostril. Such an example embodiment is shown in FIGS. 28 and 29. FIG. 28 illustrates the strap including two semi-tubular shaped bodies for securing two medical tubes, each directed into a separate nostril. FIG. 29 depicts a nostril piece for directing a single medical tube into each nostril. Similarly, Bilateral Nasal Packing, utilized predominantly post-surgeries or in mitigating nosebleeds, necessitates the strategic insertion of materials into both nostrils. Additionally, devices like the Nasal High Flow (NHF) or High Flow Nasal Cannula (HFNC) are designed to fit adeptly into both nostrils to optimize oxygen delivery. By having an interchangeable nostril piece 120, the system proffers clinicians unparalleled flexibility in tube placement and adjustment, ensuring optimal treatment delivery while enhancing patient comfort. This embodiment ensures that the apparatus can be conveniently adapted to diverse medical requirements, highlighting its broad applicability in the clinical setting.

In a second embodiment, the nostril piece 120 is integrally formed with the semi-tubular shaped body 118. It stands as a uniform body portion, indistinguishably merging with the semi-tubular shaped body, and is not designed to be separable. FIGS. 8 through 10 are detailed views (B) of FIG. 5, illustrating example embodiments of nostril pieces. The dotted lines in FIGS. 8 thorough 10 depict the nostril piece in attachment with the strap and/or the semi-tubular shaped body. Such a construction offers a streamlined and continuous design, envisaged to provide a steadfast and snug fit for the medical tube. This embodiment is particularly advantageous, perhaps even crucial, for pediatric applications, notably within neonatal and toddler care settings. Younger patients, inherently characterized by their dynamic movements and lack of full motor control, present a unique challenge in ensuring secure placement of medical tubes. A separable nostril piece in such contexts might inadvertently become disengaged due to active movement, thereby jeopardizing the tube's positioning. More gravely, a detached nostril piece, given its size and form, could potentially manifest as a choking hazard, posing a dire risk to the child's safety. Hence, by embracing a singular, non-separable design, this embodiment adeptly negates such risks, ensuring that the tube's securement remains uncompromised while simultaneously prioritizing the young patient's safety.

In yet another embodiment, the nostril piece 120 is characterized as a substantially enclosed tube, as shown in FIGS. 8 through 10. When the tube is enclosed as shown in FIG. 8, an end of the medical tube is inserted or fed into and/or through the nostril piece in the direction denoted by D1. In another example embodiment, as shown in FIG. 9, the substantially enclosed nostril piece includes at least a slit or opening to allow insertion of the medical tube while the medical tube is within the patient. As shown in FIG. 9, the nostril piece integrates an opening or slit allowing the medical tube to be inserted into the groove through the slit in the direction D2. In certain embodiments, as shown in FIG. 10, the nostril piece delineates two distinct arms (121a, 121b). These arms, equipped with resilient properties, are configured to automatically wrap around and securely clasp a tube about the groove in the directions of arrows D3, which wraps around the longitudinal axis of the groove.

These particular embodiments, shown in FIGS. 9 and 10, are especially advantageous when the medical tube is already positioned in a patient, facilitating a snug fit and streamlining the tube placement and adjustment process. Such a mechanism, reminiscent of certain self-curling materials, enhances the adaptability and user-friendliness of the nostril piece, making it an invaluable tool in varied clinical scenarios. Said embodiment allows the headpiece to be applied, adjusted, or repositioned around a patient without the need to remove, realign, or disturb the medical tube already in situ. Such a feature is particularly significant in clinical settings where removing or adjusting a medical tube might pose unnecessary risks, discomfort, or may simply be impractical. By merely unwrapping and rewrapping the arms of the nostril piece 120 around the tube, or by inserting the medical tube within the slit or groove of the nostril piece, healthcare professionals can adeptly ensure that the tube remains securely positioned while the headpiece is adjusted.

The strap may further include a cutout 122. The cutout typically denotes an area or section that has been deliberately removed, omitted, or carved out from a larger body or material, creating an aperture or void that can facilitate various functions, including but not limited to, ease of access, reduction in material weight, improved ventilation, or alleviation of localized stress or strain. In certain embodiments, the cutout is omission or void within the semi-tubular shaped body 118 of the strap. This intentional void is judiciously situated to reduce undue stress or strain on the medical tube as it contours its path around a patient's facial features. The integration of this cutout 122 not only enhances the ergonomic design of the strap but also bolsters its functional efficacy, ensuring optimal tube positioning and longevity.

The cutout is disposed within the middle portion, proximate to the confluence of the nostril piece 120 and the semi-tubular shaped body 118. The cutout is configured to alleviate undue stress or strain that the medical tube might experience as it outlines its contoured path about the semi-tubular shaped body, initiating from the nostril and curving around the facial contours. By instating this cutout 122, the strap provides a balance between assured tube securement and preserving the tube's inherent bending characteristics, forestalling any potential misshaping or occlusion. In other embodiments, particularly when the medical tubes manifest elevated pliability, the cutout 122 may be omitted. This is attributable to the innate flexibility of these tubes which can spontaneously counteract undue stress or strain without necessitating external mediations.

In one embodiment, the strap might be devoid of any cutouts, resulting in a continuous, unbroken surface about the semi-tubular shaped body. Said embodiment may be configured for medical tubes that possess inherent flexibility and thus, do not mandate stress or strain relief in the form of a cutout. Conversely, certain considerations might call for the inclusion of at least one cutout and/or multiple cutouts in the strap. This multiplicity of cutouts can cater to diverse medical tubes or varying user needs, thereby amplifying the adaptability of the head-piece in different clinical settings to adeptly secure a plurality of types of medical tubes.

In certain embodiments, the cutout 122 may be an angled recess or removal from the semi-tubular shaped body. The angled cutout is configured with an inclination or slant relative to a given reference plane or axis. This inclination is generally not perpendicular to the main plane of the body in which it resides but rather adopts an oblique orientation. This angled cutout is engineered to provide an alleviation of stress or strain on the medical tube as it transitions from the nostril region and circumnavigates the face, effectively promoting longevity of the medical tube and enhancing user comfort.

With respect to stress and strain distribution considerations, the angled cutout is configured to offer a gradient in stress and strain distribution, rather than a sudden discontinuity which a perpendicular or straight cutout might produce. This gradient transition facilitates smoother bending of the medical tube and reduces localized pressures, ensuring the tube does not undergo undue wear or potential damage, especially at the points where it interfaces with the cutout.

Additionally, with respect to ergonomic adaptability, the angled nature of the cutout promotes a more natural curve and alignment for the medical tube as it navigates the contours of the patient's face. This can enhance comfort for the patient, as the tube can nestle more organically without causing undue pressure points on the skin. Moreso, given its proximity to the nostril region of the patient, the angled cutout provides a more tailored path for the medical tube as it enters the nostril, reducing any potential kinks or sharp bends that could compromise the tube's functionality.

In particular embodiments, the strap includes a cushion 124, disposed proximate to the semi-tubular shaped body. The cushion 124 may be disposed on at least one of the first side portion and the second side portion of the strap. This cushion 124 is primarily intended to elevate user comfort by presenting a soft interface between the strap and the patient's skin, thus reducing potential discomfort, and augmenting the overall wearing experience. Noteworthily, the semi-tubular shaped body intricately adopts a serpentine path in its traversal around and in conjunction with this cushion 124. The serpentine path of the semi-tubular shaped body not only caters to the cushion's presence but also ensures that the semi-tubular shaped body intimately contours with the cushion 124, fostering the strap's stability and adaptability when worn on a patient's face.

In certain embodiments, when the cushion's curvature resonates harmoniously with the semi-tubular shaped body's own curvature, a subtle suction effect is observed at their confluence. This gentle yet effective suction aids in anchoring the positioning of the strap on the patient's cheek. Significantly, this retention is achieved without inflicting undue force or any deleterious impact on the patient's skin, underscoring the device's dedication to ensuring both patient comfort and safety.

The cushion 124 may be formulated from materials selected to optimize comfort while upholding the standards of durability and function. In one exemplary embodiment, medical-grade silicone serves as the primary material for the cushion 124, attributing to its hypoallergenic properties, tactile softness, and long-lasting resilience against routine wear. However, the cushion 124 may also be formulated from other suitable materials in alternative embodiments, including but not limited to, polyurethane, which may be used for its inherent flexibility and biocompatibility; memory foam, which may be used for its capacity to adapt to body contours and equitably distribute pressure; gel-infused padding; thermoplastic elastomers (TPE); and natural latex.

Figure 16:
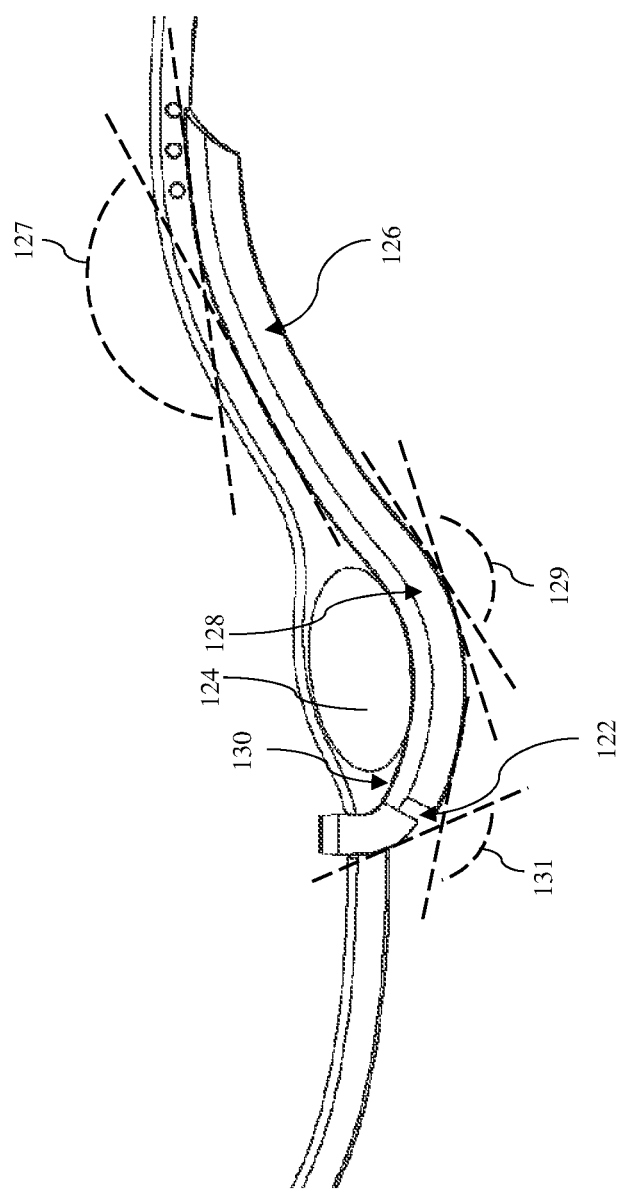
FIG. 16 is a front view of the face strap illustrating the curvature of the semi-tubular shaped body, according to an example embodiment.

Referring back to the semi-tubular shaped body 118, the semi-tubular shaped body includes a substantially straight portion 126 has an opening to the inner channel or groove. The access to the groove, as depicted in FIG. 15 is at a bottom portion of the semi-tubular shaped body, however, the access to the groove may also be on the side or top portions of the semi-tubular shaped body. This opening defines the cross-sectional shape of the semi-tubular shaft in this region. The cross-section of the open portion is unique in that it is not fully enclosed; instead, it exhibits a distinctive C-shape and/or U-shape. The curved profile of the groove allows the semi-tubular shaped body to partially enclose the channel or groove while maintaining an open arc that provides access to the channel or groove for receiving the medical tube. The channel or groove traverses from the middle portion of the strap to at least one respective side portion of the strap, terminating proximate to the backstay in an assembled configuration. The semi-tubular shaped body is a tube holder having an outer wall substantially enclosing the channel and an opening in the outer wall adjoining the channel. The channel has an ingress 118a proximate to the backstay in an assembled configuration, and an egress 118b proximate to the middle portion of the strap and/or nostril piece. As shown in FIG. 16, the semi-tubular shaped body includes a substantially straight portion 126 from the first side portion of the strap, a first curved portion 128, and a second curved portion 130. Commencing with the substantially straight portion 126, this segment purposefully extends about at least one of the first side portion or the second side portion. In its course, it effectively directs the medical tube toward the rear of the patient, ensuring an unobtrusive and streamlined tube management. The substantially straight portion is substantially straight such that the longitudinal axis of the channel within is parallel to the strap. Substantially straight means that the body may have a slight deviation away from linear, for example, to align with the curvature of the head and the natural curvature of the strap as assembled with the backstay on the patient. As shown in FIG. 16, the angle 127 of the substantially straight portion is characterized between 150 degrees to 180 degrees.

Progressing from this orientation, the substantially straight portion is contiguous to a first curved portion 128. This first curved portion is contoured to curve downward, making a deliberate arc around the cushion 124, and thereby embracing the anatomy of the patient's face. This downward curve, coupled with the cushion, enhances the wearability of the strap while minimizing any undue pressure points. The first curved portion is characterized by an angle 129 being between 90 degrees and 160 degrees.

Following the path set by the first curved portion, the semi-tubular shaped body flows into the second curved portion 130. This segment is characterized by an upward curvature arcing around the cushion 124. The second curved portion is characterized by an angle 131 being between 90 degrees and 160 degrees. Its trajectory culminates in a strategically positioned terminating end portion 132, which is situated in proximity to the middle portion of the face strap. The "terminating end portion 132 is the concluding segment of the semi-tubular shaped body. This portion marks the finite boundary of the semi-tubular shaped body, indicating where it concludes in relation to its trajectory and integration with adjoining structures, such as the nostril piece or cutout, within the face strap apparatus. This designated end portion plays a pivotal role in ensuring the proper orientation, placement, and functional integration of the semi-tubular shaped body within the overarching design and operational framework of the face strap.

With respect to the angles of the first curved portion and the second curved portion, the closer the respective curve is to 90 degrees, the more stress and/or strain on the medical tube as it contours about the face. Therefore, a cutout may be disposed between respective portions to transition the curves. In the absence of a cutout, the angle of the curvature may be more gradual and/or obtuse.

In certain embodiments, the semi tubular shaped body may be at least partially detached from the strap. This means that the semi-tubular shaped body may have at least one portion attached to the strap and at least one portion freely detached from the strap. For example, the semi-tubular shaped body may be attached to the at the substantially straight portion and at the terminating end of the second curve near the middle of the strap. Having a detached portion may allow the medical tube to naturally curve within the channel of the semi-tubular shaped body. By allowing the medical tube to naturally curve with the strap, the face of the patient will be relieved of forced pressure points on the face and stress and strain on the medical tube.

The face strap is constructed with an inherent symmetry about a frontal plane 134. The symmetrical construction of the face strap is shown in FIGS. 11 through 13, and FIG. 15. The face strap is symmetrical such that it exhibits a balanced arrangement of corresponding parts or shapes on either side of a central dividing line or about a central axis. Specifically, the face strap, in its entirety, embodies a symmetrical structure about a frontal or central plane. Such a construction implies that each half of the strap, when divided along this plane, mirrors the other in terms of structure, design, and function.

Figure 27:
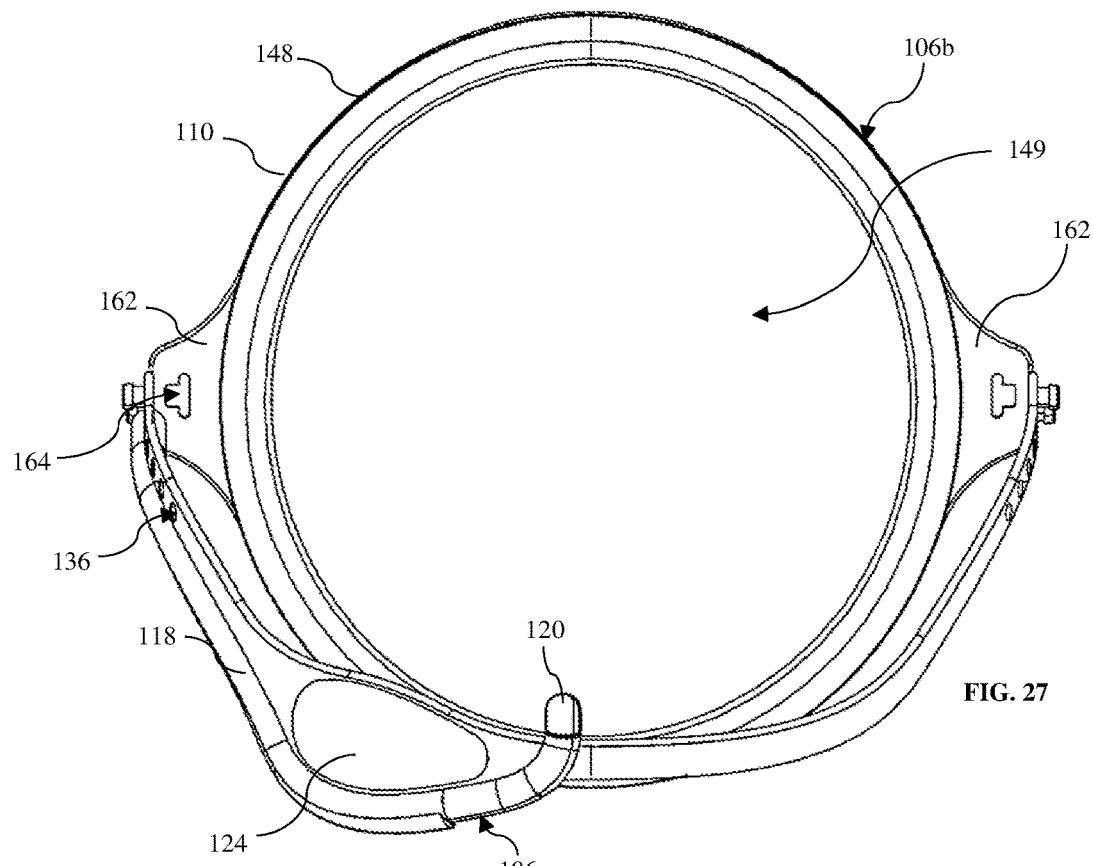
FIG. 27 is a front view of the medical tube securement system, according to another example embodiment.

For example, in the face strap may be initially orienting the first portion with the semi-tubular shaped body and groove on the right side of a patient's face, the inherent symmetry allows for a simple reorientation or a flip of the strap. By doing so, what was once the first portion on the right becomes suitably disposed on the left side of the patient's face, and vice versa. This flipping capability, stemming from its symmetrical design, ensures versatility in application, allowing caregivers and patients the flexibility to choose the side of tube placement based on patient comfort or clinical requirements, without necessitating different strap designs for left or right orientation. Additionally, by simply flipping the strap, the first portion, which was once on the right, adeptly aligns with the left side of the face and vice versa. The versatility is particularly salient in longer-term applications where periodic relief or redistribution of contact points can be paramount for patient comfort. Contrary to FIGS. 1 through 4 which show the strap, namely the semi-tubular shaped shaft disposed on the left side of the patient's face, FIG. 27 depicts the medical securement system "flipped", such that the semi-tubular shaped body may rest upon the right side of the patient's face.

The face strap further includes a plurality of fastener holes 136. Specifically, these fastener holes are strategically positioned on each of the first side portion and the second side portion. The plurality of fastener holes offers flexibility in adjustment and facilitates a tailored fit, accommodating variances in patients' facial structures and sizes.

In one embodiment, the face strap is further refined with the inclusion of a fastener 138. The fastener is detailed in FIG. 6, which is a detailed view (A) of FIG. 5. This fastener is adeptly situated in a first fastener hole 136a of the plurality of fastener holes. The provision of this fastener augments the securement capabilities of the strap, ensuring it remains steadfastly in place during use. A fastener is a device or accessory that mechanically joins or affixes two or more objects together, which as shown in FIG. 7, joins an end portion or first portion of the face strap 108a to a second portion of the face strap 108b. It is understood that the face strap has a terminating end that extends through the backstay and loops around to affix to the fastener on the strap. The primary function of a fastener is to provide a non-permanent joint, which means the joined components can be disassembled if necessary.

Figure 12:
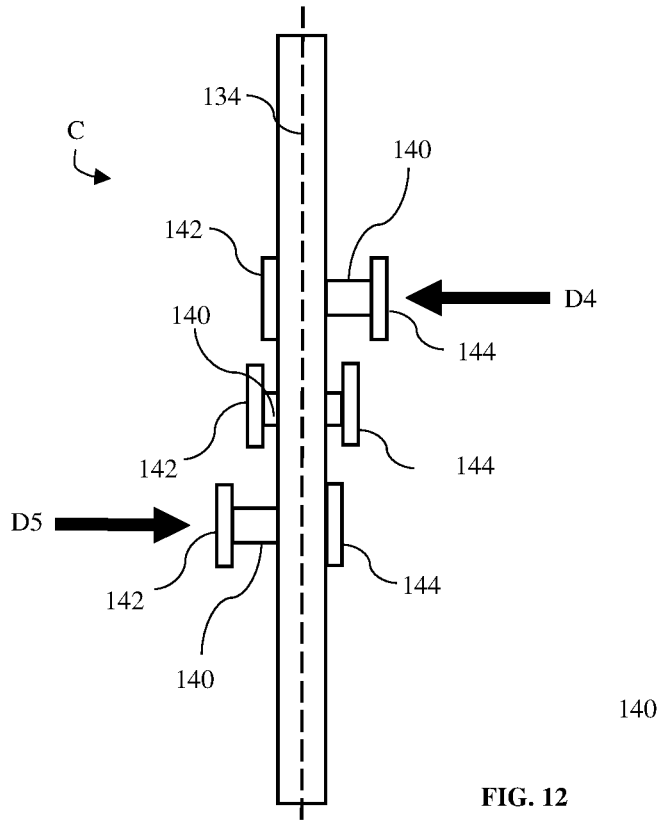
FIG. 12 is a first detailed view thereof illustrating the translational movement of the fasteners disposed in the face strap to provide dual-side application.
Figure 13:
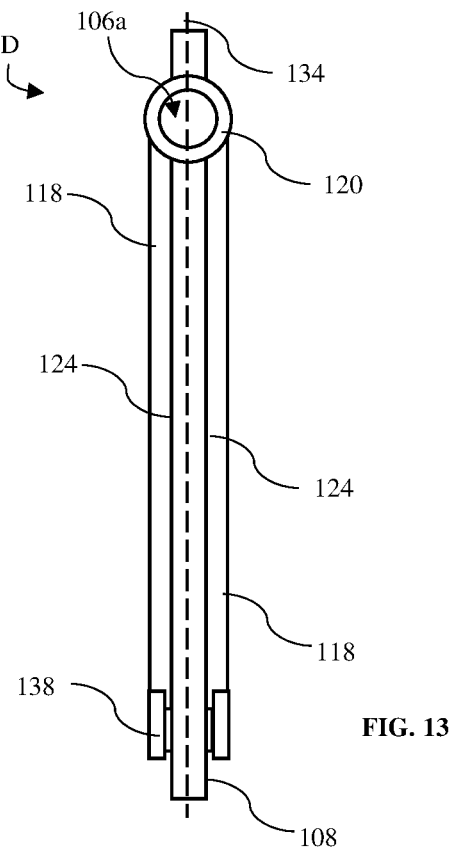
FIG. 13 is a second detailed view of thereof, according to an example embodiment.

The fastener 138, is a securing mechanism integrated into the face strap and disposed within one of the plurality of fastener holes. This fastener includes an elongated central fastener member 140 flanked by a first fastener stop 142 and a second fastener stop 144. The positioning of the fastener provides adjustable securement of the strap, thus ensuring a snug and tailored fit around a patient's face. In one exemplary embodiment, the elongated central fastener member 140 of the fastener 138 is conceived with a length that notably exceeds the width of the face strap. This permits the fastener 138 to accommodate a transverse translational movement, as denoted by the directions of the arrows D4 and D5 in FIG. 12, thus ensuring the strap remains functionally versatile and symmetrical in use. FIG. 12 is a detailed view (C) of FIG. 11. Specifically, this extended length facilitates the face strap's capability to be flipped, allowing the semi-tubular shaped body and groove to be repositioned from one side of a patient's face to the other, catering to patient comfort preferences and facilitating periodic relief from prolonged wear.

Both the first fastener stop 142 and the second fastener stop 144, situated at the extremities of the elongated central fastener member 140, play pivotal roles in the stability of the fastening system. When the fastener 138 is appropriately positioned within a selected fastener hole 136a, these stops act as barriers, effectively preventing the inadvertent disengagement or slipping of the fastener 138 from the hole. Their broader dimensions, relative to the fastener holes 136, ensure that the strap remains securely anchored, regardless of the orientation in which the strap is worn. Each of the fastener holes of the plurality of fastener holes exhibit a degree of stretchability and resilience. This allows the fastener holes, such as second fastener hole 136b, to be expanded momentarily to fit over the first fastener stop 144 or the second fastener stop 146, depending upon the orientation.

Once positioned past the stop, the second fastener hole 136b resiliently contracts, securely encompassing the elongated central fastener member 140, thereby anchoring the strap in its chosen position. This feature, in conjunction with the stops, serves to provide a double-lock mechanism, reinforcing the stability of the face strap attachment and enhancing the overall security of the device when donned by a patient.

Referring now to the backstay 110, the backstay is a structural component or element designed to provide anchoring, stabilization, or support, especially when positioned towards the rear or posterior region of the device and/or patient. This component is primarily responsible for maintaining the device's orientation, countering displacements, and ensuring user comfort by distributing tensions or loads. The backstay is a posterior anchoring component, which in operation, is coupled to the face strap. Positioned at the rear of a patient's head, the backstay 110 is adeptly designed to bear and evenly distribute the tensional forces exerted by the fastened strap, ensuring that the strap maintains its intended path and orientation around the patient's head. This tailored design minimizes localized pressure points and enhances user comfort, especially during prolonged wear, while facilitating consistent and optimal positioning of associated medical tubes or devices.

In one example embodiment, the backstay 110 is characterized by a ring-shaped body 148. This ring-shaped configuration of the body 148 is meticulously designed to encompass or encircle a portion of a patient's head or neck, offering a continuous and unified structure for enhanced support. The inherent geometry of this ring-shaped body 148 not only ensures even distribution of tensional forces arising from the strap, effectively reducing potential discomfort, but also provides facile and secure attachment points for the ends of the face strap. This construct ensures that the strap, upon fastening, retains a steadfast orientation and position, significantly diminishing any risk of inadvertent shifting or displacement during its application. Moreover, the versatile design of the ring-shaped body 148 ensures adaptability, comfortably accommodating a range of head sizes and morphologies, thus assuring user comfort across a diverse spectrum of patients.

In one embodiment, the backstay 110 is characterized by a ring-shaped body 148. The ring-shaped body is a structural entity characterized by an annular or looped arrangement, defining an inner boundary and an outer boundary, where such boundaries are predominantly equidistant from the center or the central axis of the body, creating an enclosed space or void therein. Such a ring-shaped body may circumscribe a space or area. While typically envisioned as being fully circular or looped, the term also comprehensively encompasses structures that are substantially enclosed but may have breaks, deviations, or openings in their continuity.

The ring-shaped body, is not strictly confined to a perfect circle or a specific geometric ring configuration. Instead, the ring-shaped body may include a variety of ring-like configurations and contours, whether they be oval, elliptical, teardrop-shaped, or any other substantially closed-loop shapes that might depart from a strict circular geometry. The essential characteristic of the ring-shaped body is its ability to form an annular shape, irrespective of the exact geometric form it adopts, such that it conforms to the patient's head and having a central opening 149 configured to receive a portion of the patient's head. The ring-shaped body accommodates diverse anatomical structures and user preferences, ensuring optimal fit, comfort, and utility in a broad spectrum of applications.

In contrast to prior art, the present invention introduces a ring-shaped body uniquely designed to address common shortcomings associated with prolonged wear. Notably, the ring-shaped body, having the central opening, maintains minimal contact with the user's head. Traditional headpieces often suffer from extensive surface-to-skin contact, which over time can lead to significant skin irritation and the formation of pressure sores, especially in situations demanding extended usage. The structure of the ring-shaped body in the present invention intentionally limits this surface-to-skin contact. By delineating a backstay that strategically touches only specific regions of the crown, the ring-shaped body mitigates the risk of skin irritations and pressure sores commonly induced by predecessor designs. Furthermore, this minimized contact ensures enhanced airflow, contributing to a cooler and more comfortable user experience. As such, the ring-shaped body stands as a testament to progressive design, directly addressing and ameliorating issues prevalent in the prior art, thereby augmenting the user's comfort, safety, and overall satisfaction.

This ring-shaped body 148 is configured to encompass or at least partially encircle a portion of a patient's head or neck area, offering a substantially continuous and unified structure for enhanced support. The inherent geometry of this ring-shaped body 148 not only ensures even distribution of tensional forces arising from the strap, effectively reducing potential discomfort, but also provides facile and secure attachment points for the ends of the face strap. This construct ensures that the strap, upon fastening, retains a steadfast orientation and position, significantly diminishing any risk of inadvertent shifting or displacement during its application. Moreover, the versatile design of the ring-shaped body 148 ensures adaptability, comfortably accommodating a range of head sizes and morphologies, thus assuring user comfort across a diverse spectrum of patients.

The ring-shaped body can be characterized as a halo configured to be positioned upon and comfortably rest atop the crown of a patient's head. Its structural configuration and contour, reminiscent of the universally recognized halo shape, ensures even weight distribution across the crown, minimizing localized pressure points and optimizing comfort during wear. This particular positioning, in operation, further allows for stable support and anchorage, effectively minimizing potential displacement during movements and ensuring consistent positioning of any associated apparatus or components.

In alternative embodiments, the backstay, apart from the ring-shaped body configuration, may manifest in a myriad of structural designs tailored to suit varied patient needs and ergonomic considerations. In one embodiment, the backstay 110 is conceptualized as a headband, which snugly wraps around the circumference of a patient's head, providing a stable foundation and ensuring the secure positioning of the strap on the patient's face. In another embodiment, the backstay might assume the form of a second strap that traverses the rear of the head, offering an alternative means of anchorage. Furthermore, addressing both aesthetic and functional factors, an additional embodiment envisions the ring-shaped body 148 as a structure that isn't entirely closed, resembling a tiara-like design, which rests upon the top of the head.

To optimize the stability and positioning of the backstay 110 on a patient's head, the backstay may include a textured surface 150. This surface is characterized by a plurality of protruding elements 152, meticulously arranged to enhance the overall gripping efficacy of the backstay. These protruding elements contribute to a grip-enhanced surface 154, ensuring that the backstay remains securely and comfortably positioned on the patient's head, even during potential movements or adjustments. This grip-enhanced configuration mitigates the chances of inadvertent slippage or displacement of the backstay, thus providing both clinicians and patients added assurance of the device's stability during use. The incorporation of such a textured surface not only maximizes comfort but also bolsters the overall functional efficiency of the backstay in medical applications.

Said protruding elements can be embodied in diverse configurations to both maximize grip and ensure patient comfort, including but not limited to, nubs or bumps, which are small, uniformly distributed rounded elevations providing a gentle grip; ridges, which are elongated raised sections that can run in various orientations, offering a firm grip, especially during lateral movements; waves, with their undulating design, assure a gentle yet effective grip, distributing pressure uniformly; geometrically inspired protrusions, like triangles, squares, or hexagons, combine functional grip with aesthetic appeal; and organic patterns, reminiscent of textures like tree bark or coral, present a naturally inspired grip. Alternatively, soft, flexible, brush-like bristles or comb-like teeth may be employed, especially useful for nuanced adjustments where the backstay is disposed about a patient's hair. The protruding elements on the textured surface of the backstay, designed to enhance grip when in contact with a patient's head, can be constructed from a variety of materials suitable for medical applications. Such materials include, but are not limited to, medical-grade silicone, thermoplastic elastomers (TPEs), polyurethane, and certain types of soft plastics.

These materials are chosen for their biocompatibility, ensuring that they do not induce allergic reactions or irritate the skin. Additionally, they exhibit the requisite durability and flexibility to maintain their structure and function over prolonged use, while also providing the desired grip to the patient's scalp or hair.

Referring now to FIGS. 22 through 26, in a one example embodiment, the backstay is characterized by the second groove 106b, which includes a channel 156. FIG. 23 is a cross-sectional view of FIG. 22 about line H-H. FIG. 23 illustrates a groove 106b having multiple channels 156 defining the groove and a plurality of ridges to allow for multiple wraps of the medical tube. FIG. 24 is a second embodiment of a cross-sectional view of FIG. 22 where the backstay provides a single channel having a depth suitable for a single wrap of the medical tube. FIG. 25 and FIG. 26 are detailed cross-sectional views (I) of FIG. 24 illustrating the channel and/or groove of different depths. The second groove 106b, is not fully enclosed; instead, it exhibits a distinctive C-shape and/or U-shape. The curved profile of the groove allows the semi-tubular shaped body to partially enclose the channel or groove while maintaining an open arc that provides access to the channel or groove for receiving the medical tube.

The channel is strategically disposed about a perimeter edge 158 of the ring-shaped body of the backstay. The channel is adeptly configured to receive and secure at least a portion of the medical tube 104. The particular portion of the medical tube typically pertains to the excess or additional length of the tube that generally extends towards and connects with external medical devices, equipment, or reservoirs of therapeutic agents. Such a configuration not only organizes the extra length of the medical tube, ensuring its systematic routing and preventing tangling or snagging, but also offers a stable and streamlined configuration that facilitates easy attachment and detachment to the necessary external entities.

In certain example embodiments where the backstay is said ring-shaped body, excess medical tube can be wrapped at least partially around the ring-shaped body. In other embodiments, it can undergo at least one or more wraps, contingent upon the patient's requirements or the tube's length. The channel, for added security, may incorporate a ridge 160, to ensure that the medical tube remains steadfastly positioned within the confines of the channel. A raised linear feature or protrusion present within or along a channel, specifically designed to secure, retain, or separate elements, such as a medical tube, which are placed within said channel. This ridge aids in ensuring that the element remains positioned within the channel, minimizing the risk of unintended movement or displacement.

Furthermore, in recognition of the variability in medical tubing lengths and the potential need for more organized layering, the channel in certain embodiments is deepened. This depth is designed to comfortably house multiple rounds of the medical tube around the ring-shaped body. In certain embodiments, the deepened channel may include multiple ridges, each purposed as a dedicated anchoring point, aiding in methodically organizing each successive wrap of the tube within predefined or spaced sub-channels. The use of multiple ridges assists in organizing or separating multiple wraps or layers of an element within the channel, providing systematic arrangement and stability.

In one example embodiment, the backstay may include a tab 162, or in certain configurations, at least one such tab, protruding from the backstay. In certain embodiments, the tab extends from the perimeter edge 158 of said backstay. In other embodiments, the tab may extend from a portion of the ring-shaped body. The tab includes a strap securement opening 164. The strap securement opening refers to an aperture, slot, or passage specifically designed and configured to receive, retain, or engage a strap or a portion thereof. This opening is adeptly configured to accommodate at least one of the following: a first side portion of the face strap or a second side portion of the face strap, thereby facilitating the assembly of the headpiece and its integral connection with the face strap. The specific dimensions, shape, and orientation of the strap securement opening can vary based on its intended use, the design of the strap it is intended to secure, and the overall operational requirements of the system or device in which it is incorporated.

Figure 17:
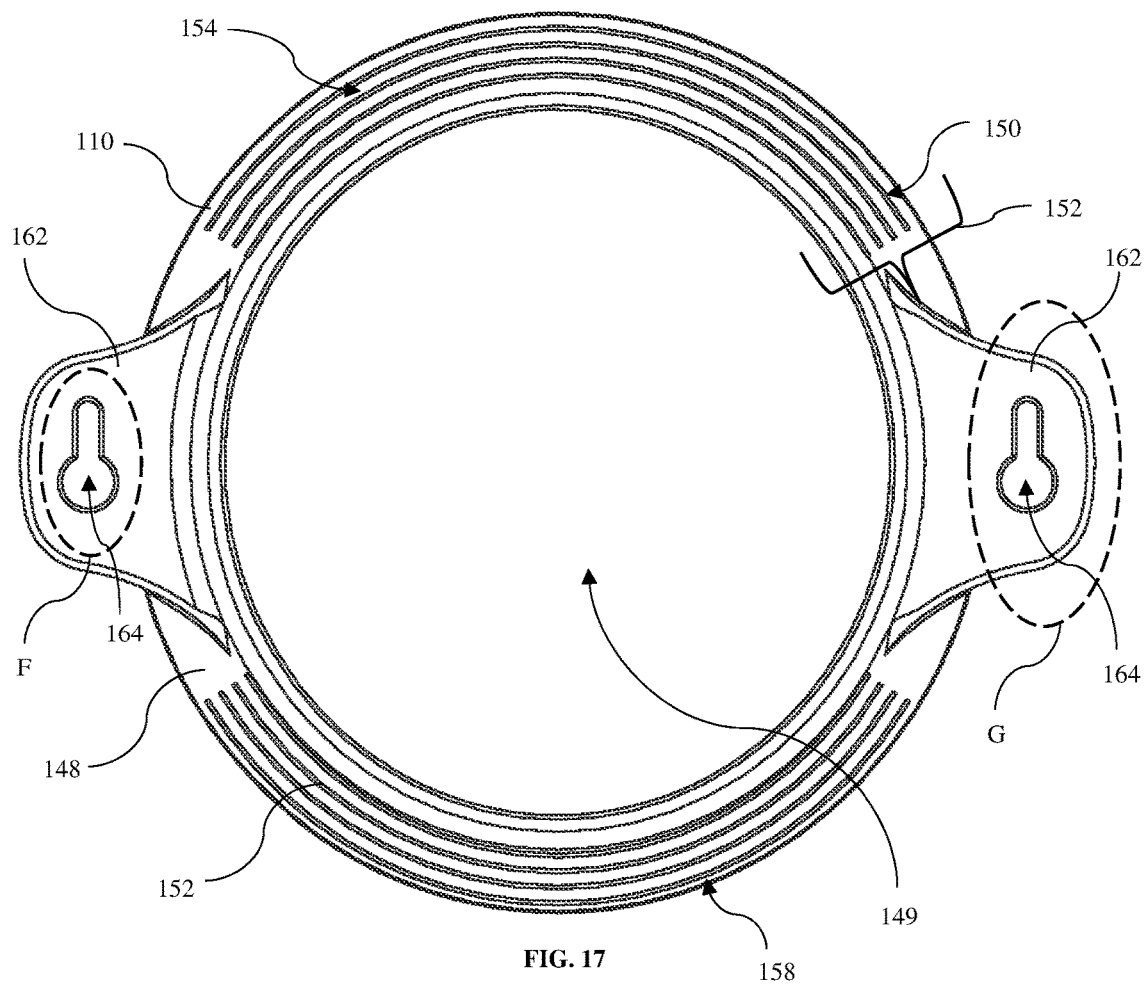
FIG. 17 is a front view of a backstay, according to an example embodiment.
Figure 18:
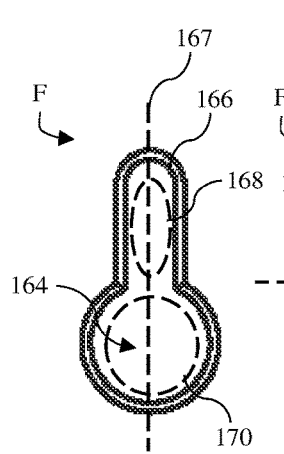
FIG. 18 is a first detailed view thereof depicting an asymmetrical transverse cross section of a strap securement opening, according to an example embodiment.
Figure 19:
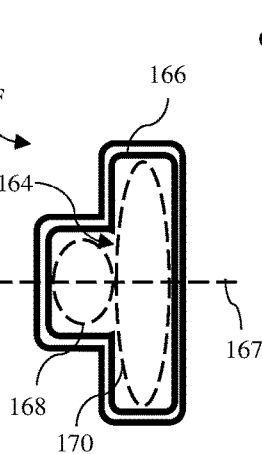
FIG. 19 is a second detailed view thereof depicting the asymmetrical transverse cross section of the strap securement opening, according to another example embodiment.
Figure 20:
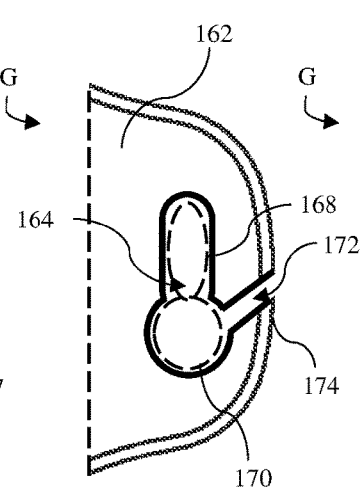
FIG. 20 is a third detailed view thereof depicting a tab having a slitted opening providing access to the strap securement opening, according to an example embodiment.

Referring now to FIGS. 18 through 21, in certain embodiments, the strap securement opening is characterized by an asymmetrical transverse cross-section 166, such that the resulting shape or configuration is not symmetrical about at least one axis 167, as to not have a mirror image about said axis. FIGS. 18 and 19 are detailed views (F) of FIG. 17, illustrating example embodiments of the asymmetrical transverse cross-section 164. The strap securement opening includes a first receiving section 168. This section has been specifically shaped and dimensioned to accommodate either the first side portion of the face strap or the second side portion of the same. Additionally, a second receiving section 170 is configured distinctively to receive and secure the medical tube. The shape and dimensions of this section have been optimized to ensure the medical tube is held in place without undue stress, strain, or potential for dislodgement. The advantage of this dual-section, asymmetrical design is evident in the enhanced organization it offers. It simplifies the assembly process of the headpiece by providing clear, separate spaces for the face strap and the medical tube. This, in turn, ensures that the components are not only efficiently secured but also organized in a manner that reduces tangling, interference, or misalignment of the headpiece.

Figure 21:
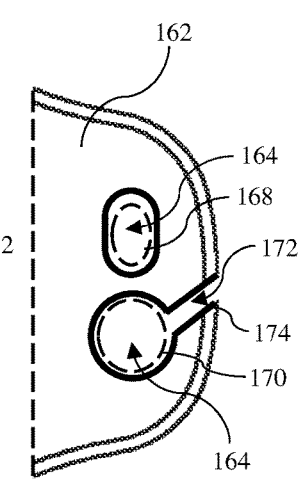
FIG. 21 is a fourth detailed view thereof depicting the tab having the slitted opening providing access to the strap securement opening, according to another example embodiment.

In another embodiment, as shown in FIGS. 21 and 22, the tab may include a slitted opening 172 that extends from a perimeter edge 174 of said tab, leading directly to the strap securement opening, or at least one of the first receiving section and the second receiving section. FIGS. 21 and 22 are detailed views (G) of FIG. 17 depicting example embodiments of the slitted opening and the strap securement opening on the tab. The slitted opening is an opening or aperture characterized by a linear cut or incision extending from one point to another on a surface or body. Such an opening may provide access, allow for the insertion, or passage of objects, or serve to facilitate specific functions related to the device or apparatus in which it is incorporated. The slitted opening provides a more user-friendly experience, especially during the process of integrating the medical tube during assembly and fitting of the headpiece.

The primary advantage of this slitted opening is that it eliminates the need to thread the end of the medical tube through the strap securement opening. Instead, users can simply slip or snap the medical tube laterally into the securement opening by way of the slit, vastly simplifying the process. This feature is particularly beneficial when the ends of the medical tube are already connected to other equipment or when the user wishes to avoid the potential complications or delays associated with threading. The presence of the slitted opening ensures that the medical tube can be efficiently and effortlessly secured while preserving its integrity and connection to any associated devices.

Overall, an exemplary method for fitting the described medical headpiece designed to organize and secure a medical tube begins with a user, such as a caregiver or patient, employing the face strap. This face strap encompasses the middle portion suitably positioned near the nostril piece, with the first and second side portions emanating from said middle portion. Notably, the semi-tubular shaped body is affixed to at least one of these side portions, adjacent to which a cushion attached thereto for enhanced comfort. To initiate the fitting, the nostril piece is meticulously aligned with the patient's nostrils, ensuring the semi-tubular shaped body contours around the cushion, thereby offering a snug fit on the patient's cheek. The medical tube is then inserted into the groove of the strap. The aforementioned side portions of the face strap are then wrapped around the patient's head towards the rear, with the semi-tubular shaped body guiding the medical tube in the desired rearward direction. Concurrently, the backstay, which can be in the form of a ring-shaped body, a headband, or a secondary strap, is readied. In scenarios where the backstay is manifested as a ring-shaped body, it is fashioned to rest atop the crown of the patient's head, and often integrates a second groove or perimeter-edged channel, purposed for the reception and organization of the medical tube's excess length. This surplus tube segment can be artfully wrapped, at least partially, around the ring-shaped body of the backstay, or in specific embodiments, multiple times. A tab extending from the backstay's perimeter edge, replete with a strap securement opening, which boasts an asymmetrical transverse cross-section, configured to receive both the side portion of the face strap and the medical tube, facilitating organized assembly of the headpiece. For enhanced security, a fastener, composed of an elongated central member flanked by stops, is utilized to anchor the face strap to the backstay. Ultimately, this method ensures that the medical tube remains in a state of organized sequestration, thereby enhancing patient comfort, promoting mobility, and obviating complications from mismanaged tubes.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

The invention claimed is:

1. A medical tube securement system for securing a nasally introduced medical tube to a patient, the medical tube securement system comprising:
    a head-piece comprising at least one groove for securing a medical tube, wherein the head-piece is non-adhesive and non-invasive, the headpiece comprising:
        an elongated face strap comprising an elongated semi-tubular shaped body spanning longitudinally along a substantial portion of a first side portion of the elongated face strap, the elongated semi-tubular shaped body comprising a substantially straight portion, a first curved portion contiguous to the substantially straight portion, and a second curved portion contiguous to the first curved portion; and
        a cushion adjacent to the elongated semi-tubular shaped body on the first side portion of the elongated face strap, wherein the first curved portion and the second curved portion curve about the cushion.

2. The medical tube securement system of claim 1, wherein the elongated face strap further comprises a cutout in the elongated semi-tubular shaped body proximate to a middle portion of the elongated face strap.

3. The medical tube securement system of claim 1, wherein the elongated face strap further comprises a plurality of fastener holes in an end portion of each of the first side portion and a second side portion.

4. The medical tube securement system of claim 3, wherein the elongated face strap further comprises a fastener disposed in a first fastener hole of the plurality of fastener holes.

5. The medical tube securement system of claim 4, wherein the fastener comprises an elongated central fastener member disposed between a first fastener stop and a second fastener stop.

6. The medical tube securement system of claim 1 wherein the elongated face strap is symmetrical about a frontal plane such that the elongated semi-tubular shaped body may be disposed on at least one of (i) a left side of a patient's face and (ii) a right side of the patient's face.

7. A medical tube securement system for securing a nasally introduced medical tube to a patient, medical tube securement system comprising:
    an elongated face strap comprising:
        an elongated semi-tubular shaped body comprising a first groove, wherein the elongated semi-tubular shaped body is disposed substantially along a side portion of the elongated face strap; and
    a backstay comprising:
        a ring-shaped body comprising a central aperture; and
        a second groove substantially around a perimeter edge of the ring-shaped body.

8. The medical tube securement system of claim 7 further comprising an operational configuration wherein the backstay is configured to be disposed on the crown of the patient's head and is coupled to the elongated face strap and wherein the nasally introduced medical tube is at least partially retained in the first groove of the elongated semi-tubular shaped body on the elongated face strap and is at least partially retained in the second groove around the backstay.

9. The medical tube securement system of claim 7, wherein the elongated face strap further comprises:
    a cushion adjacent to the elongated semi-tubular shaped body, wherein the elongated semi-tubular shaped body further comprises:

a substantially straight portion;

a first curved portion contiguous to the substantially straight portion; and a second curved portion contiguous to the first curved portion; and a relief cutout in the semi-tubular shaped body proximate to the second curved portion and a middle portion of the elongated face strap;

wherein the first curved portion and the second curved portion curve around the cushion.

10. A medical tube securement system for securing a nasally introduced medical tube to a patient, the medical tube securement system comprising:

a head-piece comprising at least one groove for securing a nasally introduced medical tube, wherein the headpiece is non-adhesive and non-invasive, the headpiece comprising:

a backstay comprising a ring-shaped body comprising a central aperture configured to retain the backstay on the crown of the patient's head; and a first groove of the at least one groove that spans substantially around a circumference of an outermost perimeter edge of the ring-shaped body configured for receiving at least a portion of the nasally introduced medical tube and retaining the at least the portion of the nasally introduced medical tube on the posterior side of the patient.

11. The medical tube securement system of claim 10 wherein the backstay comprises a tab extending outward from the backstay, wherein the tab comprises an asymmetrical transverse cross-section comprising (i) a first receiving section configured to receive a first side portion of an elongated face strap, and (ii) a second receiving section configured to receive the at least the portion of the nasally introduced medical tube.

12. The medical tube securement system of claim 11 wherein the backstay comprises a tab extending outward from the backstay, wherein the tab comprises a slitted opening extending from a perimeter edge of the tab to a strap securement opening.

13. The medical tube securement system of claim 10 wherein the first groove comprises a ridge for retaining at least a portion of the nasally introduced medical tube within the first groove and on a posterior side of the patient.

\* \* \* \* \*